United States Patent
Leotta et al.

(10) Patent No.: US 12,377,609 B2
(45) Date of Patent: Aug. 5, 2025

(54) FENESTRATION TEMPLATE FOR ENDOVASCULAR REPAIR OF AORTIC ANEURYSMS

(71) Applicant: University of Washington through its Center for Commercialization, Seattle, WA (US)

(72) Inventors: Daniel F. Leotta, Seattle, WA (US); Benjamin Starnes, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 133 days.

(21) Appl. No.: 17/198,186

(22) Filed: Mar. 10, 2021

(65) Prior Publication Data

US 2021/0187856 A1    Jun. 24, 2021

Related U.S. Application Data

(60) Division of application No. 15/724,342, filed on Oct. 4, 2017, now Pat. No. 11,052,608, which is a
(Continued)

(51) Int. Cl.
*A61F 2/07* (2013.01)
*A61F 2/95* (2013.01)
(Continued)

(52) U.S. Cl.
CPC ............. *B29C 64/386* (2017.08); *A61F 2/07* (2013.01); *A61F 2/95* (2013.01); *G05B 15/02* (2013.01);
(Continued)

(58) Field of Classification Search
CPC .......... A61F 2240/002; A61F 2240/005; A61F 2240/004; A61F 2240/007; A61F 2240/008; A61F 2/07; A61F 2/856
See application file for complete search history.

(56) References Cited

U.S. PATENT DOCUMENTS 5,370,692 A   12/1994   Fink et al.
5,607,444 A    3/1997   Lam
(Continued)

FOREIGN PATENT DOCUMENTS

CN    104240220 A    12/2014
EP     2606851 A1     6/2013
(Continued)

OTHER PUBLICATIONS

Chuter, et al. Standardized off-the-shelf components for multi-branched endovascular repair of thoracoabdominal aortic aneurysms. Perspect Vasc Surg Endovasc Ther. Sep. 2011;23(3):195-201.doi: 10.1177/1531003511430397.
(Continued)

*Primary Examiner* — Majid Jamialahmadi
(74) *Attorney, Agent, or Firm* — CHRISTENSEN O'CONNOR JOHNSON KINDNESS PLLC

(57) ABSTRACT

To provide simple yet accurate stent graft fenestration, a patient-specific fenestration template is used as a guide for graft fenestration. To generate the fenestration template, a patient's medical imaging data such as CT scan data may be used to generate a 3-D digital model of an aorta lumen of the patient. The aorta lumen may encompass one or more branch vessels, which may be indicated on the 3-D digital model. Based on the 3-D digital model or a segment thereof, the fenestration template may be generated, for example, using 3-D printing technology. The fenestration template may include one or more holes or openings that correspond to the one or more branch vessels. To fenestrate a stent graft, the fenestration template is coupled to the stent graft so that the holes or openings on the fenestration template indicate the fenestration locations.

10 Claims, 16 Drawing Sheets

Related U.S. Application Data continuation of application No. 13/875,209, filed on May 1, 2013, now Pat. No. 9,811,613.

(60) Provisional application No. 61/641,183, filed on May 1, 2012.

(51) Int. Cl.

| | |
|---|---|
| *B29C 64/386* | (2017.01) |
| *G05B 15/02* | (2006.01) |
| *G06F 30/20* | (2020.01) |
| *G09B 23/30* | (2006.01) |
| *A61F 2/06* | (2013.01) |
| *A61F 2/89* | (2013.01) |
| *B29C 64/10* | (2017.01) |
| *B33Y 50/02* | (2015.01) |
| *B33Y 80/00* | (2015.01) |

(52) U.S. Cl.
CPC .............. *G06F 30/20* (2020.01); *G09B 23/30* (2013.01); *A61F 2002/061* (2013.01); *A61F 2/89* (2013.01); *A61F 2230/0054* (2013.01); *A61F 2240/002* (2013.01); *A61F 2240/005* (2013.01); *B29C 64/10* (2017.08); *B33Y 50/02* (2014.12); *B33Y 80/00* (2014.12)

(56) References Cited

U.S. PATENT DOCUMENTS

| | | |
|---|---|---|
| 5,984,955 A | 11/1999 | Wisselink |
| 6,030,414 A | 2/2000 | Taheri |
| 6,036,702 A | 3/2000 | Bachinski et al. |
| 6,059,824 A | 5/2000 | Taheri |
| 6,395,018 B1 | 5/2002 | Castaneda |
| 6,524,335 B1 | 2/2003 | Hartley et al. |
| 6,616,675 B1 | 9/2003 | Evard et al. |
| 6,719,768 B1 | 4/2004 | Cole et al. |
| 7,197,170 B2 | 3/2007 | Dwyer et al. |
| 7,306,623 B2 | 12/2007 | Watson |
| 7,306,633 B2 | 12/2007 | Wilz |
| 7,413,573 B2 | 8/2008 | Hartley et al. |
| 7,833,266 B2 | 11/2010 | Gregorich et al. |
| 7,937,660 B2 | 5/2011 | Binkert |
| 8,216,298 B2 | 7/2012 | Wright et al. |
| 8,287,586 B2 | 10/2012 | Schaeffer et al. |
| 8,337,547 B2 | 12/2012 | Iancea et al. |
| 8,359,118 B2 | 1/2013 | Ono et al. |
| 8,682,626 B2 | 3/2014 | Ionasec et al. |
| 8,682,686 B2 | 3/2014 | Warner et al. |
| 8,808,351 B2 | 8/2014 | Osborne |
| 8,831,302 B2 | 9/2014 | Mahfouz |
| 8,897,513 B2 | 11/2014 | Balasubramanian |
| 8,945,202 B2 | 2/2015 | Mayberry et al. |
| 8,958,623 B1 | 2/2015 | Grady et al. |
| 8,989,460 B2 | 3/2015 | Mahfouz |
| 9,125,733 B2 | 9/2015 | Greenberg et al. |
| 9,259,336 B2 | 2/2016 | Schaeffer et al. |
| 9,305,123 B2 | 4/2016 | Leotta et al. |
| 9,694,108 B2 | 7/2017 | Cully et al. |
| 9,724,187 B2 | 8/2017 | Ivancev et al. |
| 9,737,394 B2 | 8/2017 | Coghlan et al. |
| 9,801,741 B1 | 10/2017 | Thapliyal |
| 9,811,613 B2 | 11/2017 | Leotta et al. |
| 9,888,971 B2 | 2/2018 | Taylor |
| 9,905,421 B2 | 2/2018 | Ok et al. |
| 10,004,616 B2 | 6/2018 | Chakfe et al. |
| 10,603,196 B2 | 3/2020 | Mayberry et al. |
| 2002/0042564 A1 | 4/2002 | Cooper et al. |
| 2002/0042622 A1 | 4/2002 | Vargas et al. |
| 2002/0095205 A1 | 7/2002 | Edwin et al. |
| 2002/0193872 A1 | 12/2002 | Trout et al. |
| 2003/0093145 A1 | 5/2003 | Lawrence-Brown et al. |
| 2004/0034406 A1 | 2/2004 | Thramann |
| 2004/0059406 A1 | 3/2004 | Cully et al. |
| 2004/0064081 A1 | 4/2004 | Stanish |
| 2004/0102866 A1 | 5/2004 | Harris et al. |
| 2004/0116997 A1* | 6/2004 | Taylor ...................... A61F 2/07 623/1.13 |
| 2004/0138737 A1 | 7/2004 | Davidson et al. |
| 2005/0102021 A1 | 5/2005 | Osborne |
| 2005/0131517 A1 | 6/2005 | Hartley et al. |
| 2005/0131518 A1 | 6/2005 | Hartley |
| 2005/0137518 A1 | 6/2005 | Biggs et al. |
| 2005/0149166 A1 | 7/2005 | Schaeffer et al. |
| 2005/0171598 A1 | 8/2005 | Schaeffer |
| 2006/0058638 A1 | 3/2006 | Boese et al. |
| 2006/0116749 A1 | 6/2006 | Willink et al. |
| 2006/0155359 A1 | 7/2006 | Watson |
| 2006/0259116 A1 | 11/2006 | Feld et al. |
| 2007/0142900 A1 | 6/2007 | Balaji |
| 2007/0244547 A1 | 10/2007 | Greenan |
| 2007/0293936 A1 | 12/2007 | Dobak |
| 2007/0293940 A1 | 12/2007 | Schaeffer et al. |
| 2008/0109066 A1 | 5/2008 | Quinn |
| 2008/0147174 A1 | 6/2008 | Konstantino et al. |
| 2008/0201007 A1 | 8/2008 | Boyden et al. |
| 2008/0255582 A1 | 10/2008 | Harris |
| 2009/0030502 A1 | 1/2009 | Sun et al. |
| 2009/0204228 A1 | 8/2009 | Hiles |
| 2009/0264990 A1 | 10/2009 | Bruszewski et al. |
| 2009/0304245 A1 | 12/2009 | Egger et al. |
| 2010/0063576 A1 | 3/2010 | Schaeffer et al. |
| 2010/0121429 A1 | 5/2010 | Greenan et al. |
| 2010/0268319 A1 | 10/2010 | Bruszewski et al. |
| 2011/0054586 A1 | 3/2011 | Mayberry et al. |
| 2011/0060446 A1 | 3/2011 | Ono et al. |
| 2011/0270378 A1 | 11/2011 | Bruszewski et al. |
| 2011/0295364 A1 | 12/2011 | Konstantino et al. |
| 2012/0010711 A1* | 1/2012 | Antonyshyn ......... B29C 51/265 425/395 |
| 2012/0035714 A1 | 2/2012 | Ducke et al. |
| 2012/0046728 A1 | 2/2012 | Huser et al. |
| 2013/0116775 A1 | 5/2013 | Roeder et al. |
| 2013/0282102 A1 | 10/2013 | Peterson et al. |
| 2013/0289690 A1* | 10/2013 | Thapliyal ................. A61F 2/90 53/425 |
| 2013/0296998 A1 | 11/2013 | Leotta et al. |
| 2013/0338760 A1 | 12/2013 | Aristizabal et al. |
| 2014/0180393 A1 | 6/2014 | Roeder |
| 2014/0277335 A1 | 9/2014 | Greenberg et al. |
| 2014/0350658 A1 | 11/2014 | Benary et al. |
| 2015/0005868 A1 | 1/2015 | Koskas et al. |
| 2015/0073534 A1 | 3/2015 | Roeder et al. |
| 2015/0216686 A1 | 8/2015 | Chakfe et al. |
| 2015/0230916 A1 | 8/2015 | Ivancev et al. |
| 2015/0234957 A1 | 8/2015 | Leotta et al. |
| 2016/0022450 A1 | 1/2016 | Hehrlein |
| 2016/0232667 A1 | 8/2016 | Taylor |
| 2017/0112642 A1 | 4/2017 | Hartley et al. |
| 2018/0153680 A1 | 6/2018 | Greenberg et al. |
| 2018/0243076 A1 | 8/2018 | Greenberg et al. |
| 2019/0050507 A1 | 2/2019 | Leotta et al. |
| 2019/0336311 A1 | 11/2019 | Schaeffer et al. |

FOREIGN PATENT DOCUMENTS

| | | |
|---|---|---|
| WO | 20020229758 A2 | 4/2002 |
| WO | 20020229758 A3 | 4/2003 |
| WO | 03099108 A2 | 12/2003 |
| WO | 2005034810 A1 | 4/2005 |
| WO | 2007045000 A2 | 4/2007 |
| WO | 2008124222 A1 | 10/2008 |
| WO | 2010024867 A1 | 3/2010 |
| WO | 2010024880 A1 | 3/2010 |
| WO | 2010030370 A1 | 3/2010 |
| WO | 2010127040 A1 | 11/2010 |

OTHER PUBLICATIONS

Chuter, Fenestrated and Branched Stent-Grafts for Thoracoabdominal, Pararenal and Juxtarenal Aortic Aneurysm Repair. Semin Vase Surg. 2007; 20:90-96.

(56) References Cited

OTHER PUBLICATIONS

Elkouri, et al. Most patients with abdominal aortic aneurysm are not suitable for endovascular repair using currently approved bifurcated stent-grafts. Vasc Endovascular Surg. Sep. 2004-Oct. 38(5):401-12.

Hazer, et al. A workflow for computational fluid dynamics simulations using patient-specific aortic models. 24th CADFEM users meeting 2006. International Congress on FEM technology with 2006 German ANSYS Conference.

Higashiura, et al. Initial experience of branched endovascular graft for abdominal aortic aneurysm with complex anatomy of proximal neck: planning and technical considerations. Jpn J Radial. Jan. 2010;28(1):66-74. doi: 10.1007/s11604-009-0381-9. Epub Jan. 30, 2010.

Legget, et al. System for quantitative three-dimensional echocardiography of the left ventricle based on a magnetic-field position and orientation sensing system. IEEE Transactions on Biomedical Engineering. 1998; 45(4):494-504.

Leotta, et al. Measurement of abdominal aortic aneurysms with three-dimensional ultrasound imaging: preliminary report. J Vasc Surg. Apr. 2001;33(4):700-7.

Malina, et al. EVAR and complex anatomy: an update on fenestrated and branched stent grafts. Scand J Surg. 2008;97(2):195-204.

Nordon, et al. Toward an off-the-shelf fenestrated endograft for management of short-necked abdominal aortic aneurysms: an analysis of current graft morphological diversity. J Endovasc Ther. Feb. 2010;17(1):78-85. doi: 10.1583/09-2895R.1.

Notice of Allowance dated Jul. 5, 2017 for U.S. Appl. No. 13/875,209.

Oderich, et al. Modified fenestrated stent grafts: device design, modifications, implantation, and current applications. Perspect Vasc Surg Endovasc Ther. Sep. 2009;21(3):157-67. doi: 10.1177/1531003509351594. Epub Dec. 3, 2009.

Office Action dated Sep. 20, 2016 from U.S. Appl. No. 15/163,255, 10 pages.

Office Action dated Feb. 22, 2017 for U.S. Appl. No. 13/875,209.

Office Action dated Mar. 9, 2016 for U.S. Appl. No. 13/875,209.

Office Action dated Sep. 8, 2016 for U.S. Appl. No. 13/875,209.

Resch, et al. Incidence and management of complications after branched and fenestrated endografting. J Cardiovasc Surg (Torino). Feb. 2010;51(1):105-13.

Ricotta, et al., "Fenestrated and branched stent grafts. Perspect Vasc Surg Endovasc Ther," Jun. 20, 2008 (2):174-87; discussion 188-9. doi: 10.1177/1531003508320491.

Stratasys, et al., "Dimension 1200es 3D modeling printer. Durability meets affordability," 2014.

UK EVAR trial investigators. Endovascular versus open repair of abdominal aortic aneurysm. N Engl J Med. May 20, 2010;362(20):1863-71. doi: 10 .1056/NEJMoa0909305. Epub Apr. 11, 2010.

Notice of Allowance dated Jan. 29, 2016 for U.S. Appl. No. 14/701,382.

Office Action dated Jul. 30, 2015 for U.S. Appl. No. 14/701,382.

\* cited by examiner

FENESTRATION TEMPLATE FOR ENDOVASCULAR REPAIR OF AORTIC ANEURYSMS

CROSS-REFERENCES TO RELATED APPLICATIONS

This application is a divisional of U.S. application Ser. No. 15/724,342, filed Oct. 4, 2017, which claims priority to U.S. application Ser. No. 13/875,209, filed May 1, 2013 (now U.S. Pat. No. 9,811,613), which claims the benefit of U.S. Provisional Application No. 61/641,183, filed May 1, 2012, each of which are incorporated herein by reference.

BACKGROUND OF THE INVENTION

Aneurysms generally involve the abnormal swelling or dilation of a blood vessel such as an artery. The wall of the abnormally dilated blood vessel is typically weakened and susceptible to rupture. For example, an abdominal aortic aneurysm (AAA) is a common type of aneurysm that poses a serious health threat. A common way to treat AAA and other types of aneurysm is to place an endovascular stent graft such that the stent graft spans across and extends beyond the proximal and distal ends of the diseased portion of the vasculature. The stent graft is designed to reline the diseased vasculature, providing an alternate blood conduit that isolates the aneurysm from the high pressure flow of blood, thereby reducing or eliminating the risk of rupture.

Minimally invasive endovascular repair using stent grafts is often preferred to avoid the risks associated with traditional open surgical repair. However, these stent grafts can only be used when the graft can be placed in a stable position without covering major branch vessels. In the cases of juxtarenal aneurysm where the dilation extends up to but does not involve the renal arteries, the proximal portion of the stent graft needs to be secured to the aortic wall above the renal arteries, thereby blocking the openings to the renal arteries. Thus, patients with juxtarenal aneurysms, which represent a significant proportion of abdominal aortic aneurysm cases, are typically excluded from endovascular treatment.

To allow for endovascular repair of a wider range of cases, surgeons sometimes cut openings in the stent graft body to accommodate specific branch vessel origins, a process known as "fenestration". Thus, for example, in treating juxtarenal aneurysms, the fenestrations or openings of the stent grafts are to be aligned with the renal arteries. Traditionally, the fenestration process involves measurements based on medical images (such as CT scans) of the vessel origins. Longitudinal distances may be measured, and relative angular locations may be estimated from a reference point.

However, these manual measurements may take a substantial amount of time and effort, particularly when multiple branch vessels must be accommodated. For example, in abdominal aortic aneurysms, fenestrations may be required for both left and right renal arteries, the superior mesenteric artery (SMA), and the celiac artery. In addition, approximations of the placement of the branch openings could lead to errors in the placement of the openings compared to the true branch vessel origins. In some cases, openings may be erroneously placed over stent struts. Therefore, there is a need for a simple yet accurate and cost-effective way to obtain fenestrated stent grafts.

SUMMARY OF THE INVENTION

Devices and methods for improving the fenestration process of stent grafts are provided. According to one aspect of the invention, a fenestration template device for an aortic graft is provided. The device comprises a physical model representing a section of a patient's aorta having one or more branch vessel openings, the physical model comprising a wall defining a lumen and having one or more openings in the wall representing the one or more branch vessel openings of the patient's aorta. The physical model is generated using a three-dimensional (3-D) printing technology. The one or more openings in the wall are indicative of locations of one or more fenestrations on the stent graft when the fenestration template device is coupled with the aortic graft. The physical model may be disposable.

According to another aspect of the invention, a method is provided for fenestrating a stent graft to be used in treating a patient. The method comprises obtaining a fenestration template generated based at least in part on a 3-D digital model of an aorta lumen of the patient, the fenestration template comprising one or more openings corresponding to one or more branch vessels encompassed by the aorta lumen and generating one or more fenestrations on the stent graft according to the fenestration template. The fenestration template may be generated using an additive prototyping technology. The 3-D digital model may be generated based at least in part on imaging data of the patient. Furthermore, generating the one or more fenestrations on the stent graft includes coupling the fenestration template with the stent graft and identifying locations of the one or more fenestrations based at least in part on the one or more openings of the fenestration template.

According to another aspect of the invention, a computer-implemented method is provided for generating a patient-specific fenestration template. The method comprises receiving imaging data of a patient, generating, based at least in part on the imaging data, a 3-D digital model of an aorta lumen of a patient, the aorta lumen encompassing one or more branch vessels, and causing generation of a fenestration template based at least in part on the 3-D digital model. The imaging data may include at least CT scan data, ultrasound data, or MRI data. Generating the 3-D digital model of the aorta lumen may include providing indications of the one or more branch vessels on the 3-D digital model based at least in part on the imaging data. Causing generation of the fenestration template may include converting the 3-D digital model to a solid object model format suitable for 3-D printing.

According to another aspect of the invention, a method is provided for treating aortic aneurysm. The method comprises obtaining a stent graft comprising one or more fenestrations generated using a fenestration template, the fenestration template generated based on a 3-D digital model of an aorta lumen of a patient, and deploying the stent graft in the aorta lumen of the patient such that the one or more fenestrations accommodate one or more branch vessels encompassed by the aorta lumen. The fenestration template may comprise one or more openings corresponding to the one or more branch vessels and the fenestration template may be manufactured using 3-D printing technology.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

This present technology takes advantage of 3-D image reconstruction and rapid prototyping technology to produce custom devices that improve patient care. The present technology includes an accurate and cost-effective means to modify a standard off-the-shelf aortic stent graft to preserve branch vessels for treatment of patients with juxtarenal aortic aneurysms. The disclosed methods provide accurate placement of the fenestrations by reproducing the true anatomy of each patient in a custom template. Specific measurements of distances and angles by surgeons are not required because the fenestration locations are defined by the 3-D computer model.

In some embodiments, a patient's imaging data (such as CT data) is used to generate a 3-D model of the patient's aorta lumen encompassing one or more branch vessels. The 3-D model may include indication of the locations of the one or more branch vessels origins. Based on the 3-D model or a segment thereof, a fenestration template may be produced such as by using 3-D printing technology. The fenestration template may include one or more openings at the locations of the branch vessel origins. To fenestrate a stent graft, the fenestration template may be coupled to the stent graft (e.g., by slipping the fenestration template over the stent graft). The relative positions of the fenestration template and/or the stent graft may be adjusted to avoid placing a fenestration on a stent strut. The fenestrations on the stent graft can be cut with the fenestration template in place, or their locations can be marked with a sterile pen and cut with the fenestration template removed.

Because the fenestration template is generated from images of each patient's aorta, the template assures accurate angular and longitudinal placement of the fenestrations to match the aorta branch vessels. Time is saved both in pre-operative planning, and also in the operating room because the relative distances of the openings are established by the template: the surgeon is not required to perform any measurements at the time of device deployment.

As used herein, proximal portion of an aorta or a stent graft refers to a portion of the aorta or the stent graft that is closer to the heart and distal portion of an aorta or a stent graft refers to a portion of the aorta or the stent graft that is further away from the heart.

Figure 1:
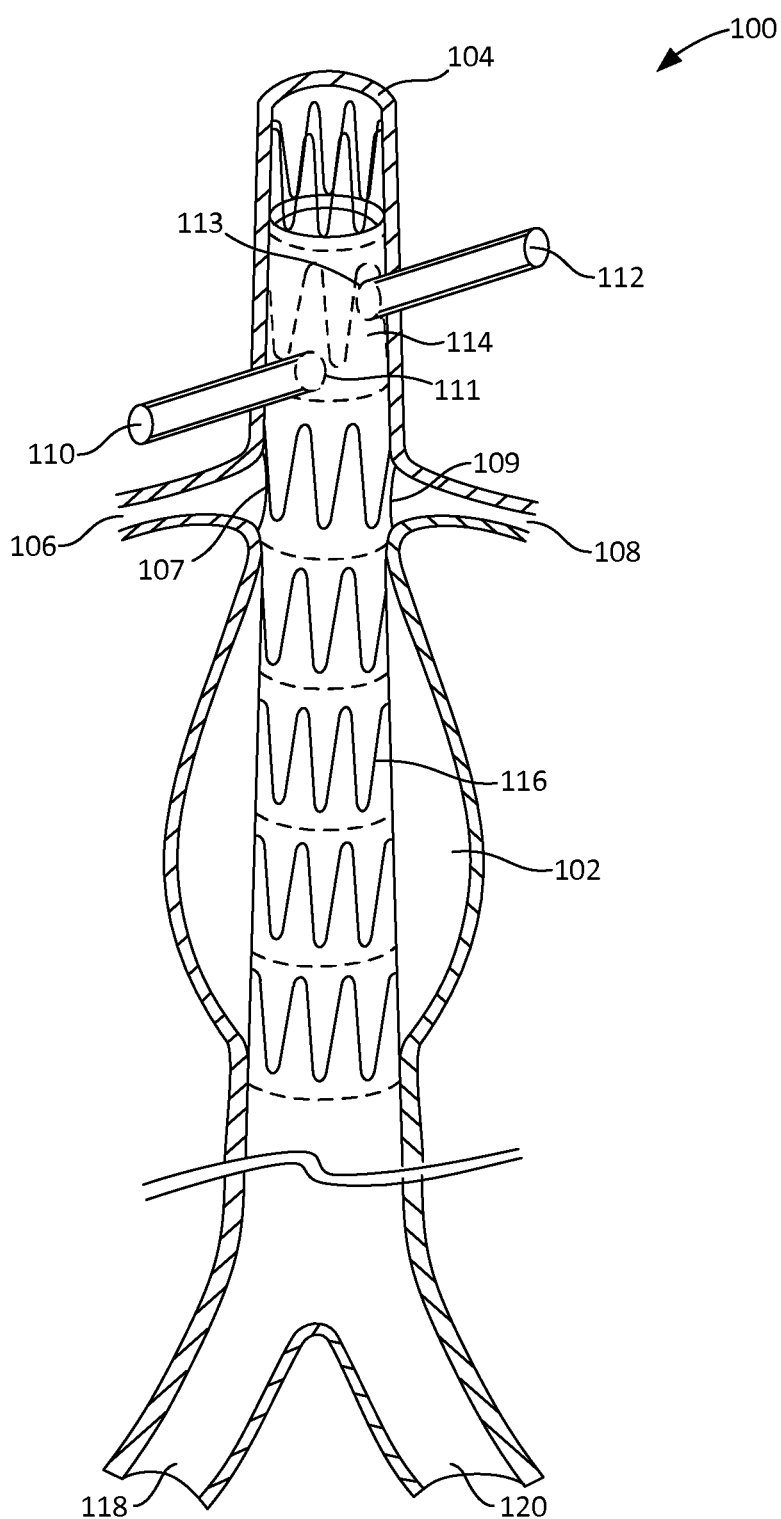
FIG. 1 illustrates an example stent graft deployed in an abdominal aorta, in accordance with at least one embodiment.

FIG. 1 illustrates an example stent graft 100 deployed in an abdominal aorta, in accordance with at least one embodiment. As shown, the stent graft is deployed inside an aorta 104 to treat an aneurysm 102 that extends from below the renal arteries 106 and 108. The stent graft typically has a tubular body and comprises a plurality of internal 114 and/or external 116 stents or stent-like structures (collectively referred to as stent struts) supporting a graft material that is typically biocompatible. In some cases, the stent graft may have bifurcated legs extending into one or more additional branch vessels such as iliac arteries 118 and 120.

In some cases, the stent graft needs to provide fenestrations (holes) to allow blood flow through the stent graft into side branch vessels. For example, in cases involving juxarenal aneurysms, the non-dilated portion of the aorta proximal to the aneurysm is typically too short to provide a reliable seal between the stent graft and the aorta. In such cases, the proximal end of the stent graft needs to be placed higher in the non-dilated portion of the aorta. Thus, as shown in FIG. 1, the proximal portion of the stent graft needs to provide fenestrations such as 107 and 109 to allow flow through the stent graft into the renal arteries 106 and 108, respectively. Preferably, the locations of the fenestrations are selected to avoid overlapping with the stent struts. Depending on the deployment position of the stent graft, in some cases, the stent graft may also include additional fenestrations such as 111 and 113 to accommodate other branch vessels such as superior mesenteric artery (SMA) 110 and celiac artery 112.

Generally, a precise fit between the fenestrations of the stent graft and the openings of the branch vessels is important both for ensuring the flow between the aorta and the branch vessels and for excluding the flow to the aneurysm. To ensure a precise fit, a stent graft for a particular patient is preferably fenestrated accordingly to that patient's particular anatomy.

Figure 2:
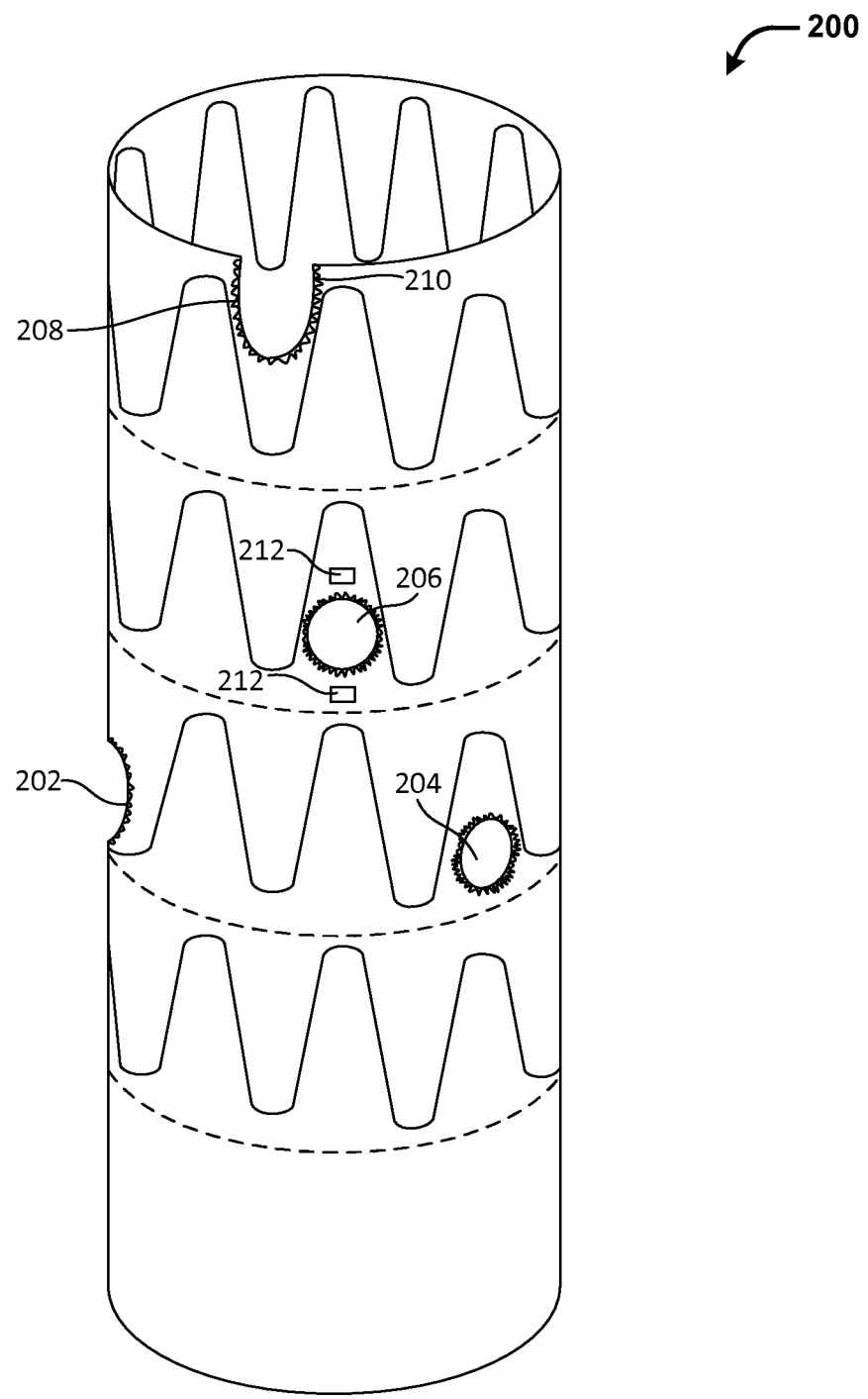
FIG. 2 illustrates an example fenestrated portion of a stent graft, in accordance with at least one embodiment.

FIG. 2 illustrates an example fenestrated portion 200 of a stent graft, in accordance with at least one embodiment. As discussed above, a stent graft may include one or more fenestrations configured to accommodate one or more branch vessels when the stent graft is deployed in an aorta. A fenestrated portion of the stent graft includes at least one fenestration. The fenestrated portion may be located near a proximal end, a distal end or any portion of the stent graft where branch vessels need to be accommodated. In this example, the fenestrated portion of the stent graft includes two fenestrations 202 and 204, each corresponding to a renal artery. The fenestrated portion may include additional fenestrations for other branch vessels that may be otherwise blocked by the unfenestrated stent graft. For example, the fenestrated portion 200 includes fenestrations 206 and 208 to accommodate the superior mesenteric artery (SMA) and celiac artery, respectively. In other embodiments, a stent graft may include fenestrations to accommodate more or fewer branch vessels than illustrated here. For example, a stent graft may include fenestrations to accommodate the inferior mesenteric artery (IMA), internal iliac arteries, and the like.

In various embodiments, the fenestrations in a stent graft may be of any suitable sizes or shapes. In typical embodiments, the fenestrations are sized and/or shaped to accommodate the corresponding branch vessel openings. For example, the fenestrations may be substantially circular if the corresponding branch vessel is otherwise covered entirely by the graft material of the deployed stent graft. Such may be the case when the branch vessels are located away from the ends of the stent grafts. For example, as shown, fenestrations 206 and 208 for the renal arteries are substantially circular. On the other hand, the fenestration may be partially circular if the corresponding branch vessel is only partially covered by the graft material during deployment. Such may be the case when the branch vessels are located near an end of the stent grafts. For example, as shown, fenestration 202 for the celiac artery is only partially circular or U-shaped to accommodate only a portion of branch vessel opening that is blocked by the graft material. In yet other embodiments, the fenestrations may have non-circular shapes.

In various embodiments, the peripherals of the fenestrations may be reinforced wholly or partially to provide stability, for example, for anchoring of stent grafts into the branch vessels. In an embodiment, the peripheral of a fenestration may be stitched or sutured using wires. In another embodiment, the peripheral of a fenestration may be coupled (e.g., via stitches) to a ring or a similar support frame.

In various embodiments, the fenestrations may be marked to facilitate location of the fenestrations during deployment of the stent graft. For example, the peripheral of the fenestrations may be sutured using gold wires 210 or wires of other radio-opaque materials. Similarly, the location of the fenestration may be marked by one or more radio-opaque markers 212. Such radio-opaque wires or markers may facilitate fluoroscopic visualization of the fenestrations during the repair procedure and allow a physician to locate the fenestration with respect to the corresponding branch vessel.

Figure 3:
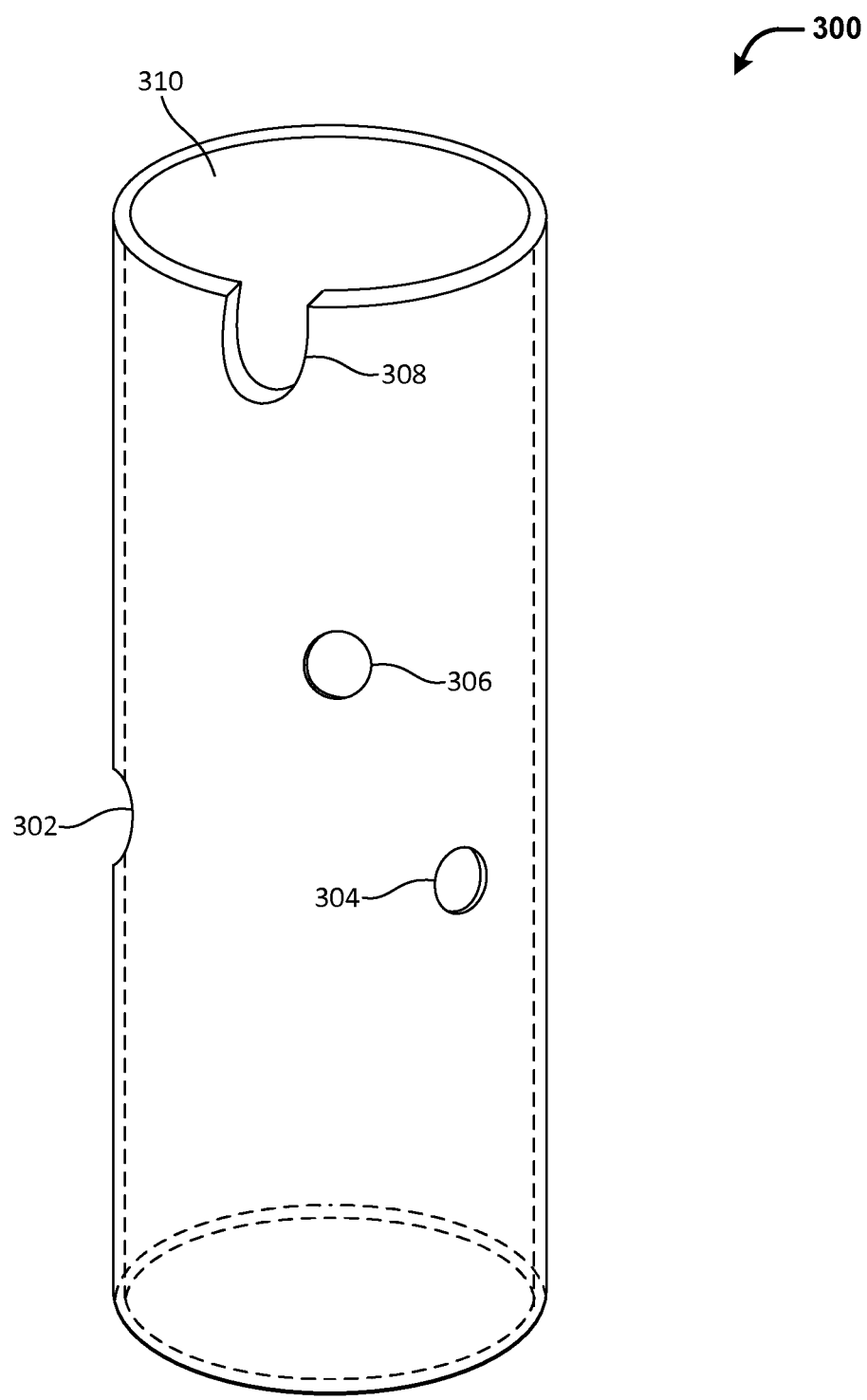
FIG. 3 illustrates an example fenestration template that may be used to generate fenestrations on a stent graft, in accordance with at least one embodiment.

FIG. 3 illustrates an example fenestration template 300 that may be used to generate fenestrations on a stent graft, in accordance with at least one embodiment. For example, the fenestration template 300 may be used to generate fenestrations illustrated in FIG. 2. The fenestration template typically includes one or more branch openings corresponding to the openings of one or more branch vessels in an aorta. As illustrated, the fenestration template 300 includes branch openings 302 and 304 for the renal arteries as well as openings 306 and 308 for the SMA and celiac artery, respectively. The diameters of the branch openings on the fenestration template may correspond to the diameters of actual openings of branch vessels in a patient's aorta, or may be of a predefined value (e.g., 4 mm). In other embodiments, the fenestration template may include more or fewer branch openings than illustrated here.

Generally, the shape of the fenestration template corresponds to the lumen of an aorta segment that encompasses one or more branch vessels. Hence, the fenestration templates typically have a tubular or cylindrical shape. In some embodiments, such as illustrated in FIG. 3, the fenestration template may include a lumen 310 that corresponds to the lumen of an aorta. The diameter of the lumen 310 may be determined based on a diameter of the stent graft to be used with the fenestration template or a predefined value. When in use, in some embodiments, the fenestration template may be slid over a stent graft such that the stent graft is at least partially inside the lumen of the fenestration template. In other embodiments, the stent graft may be slid over the fenestration template such that the fenestration template is at least partially inside the lumen of the stent graft. In either case, the fenestration template is configured to overlap with a portion of the stent graft where fenestration is required.

Figure 4:
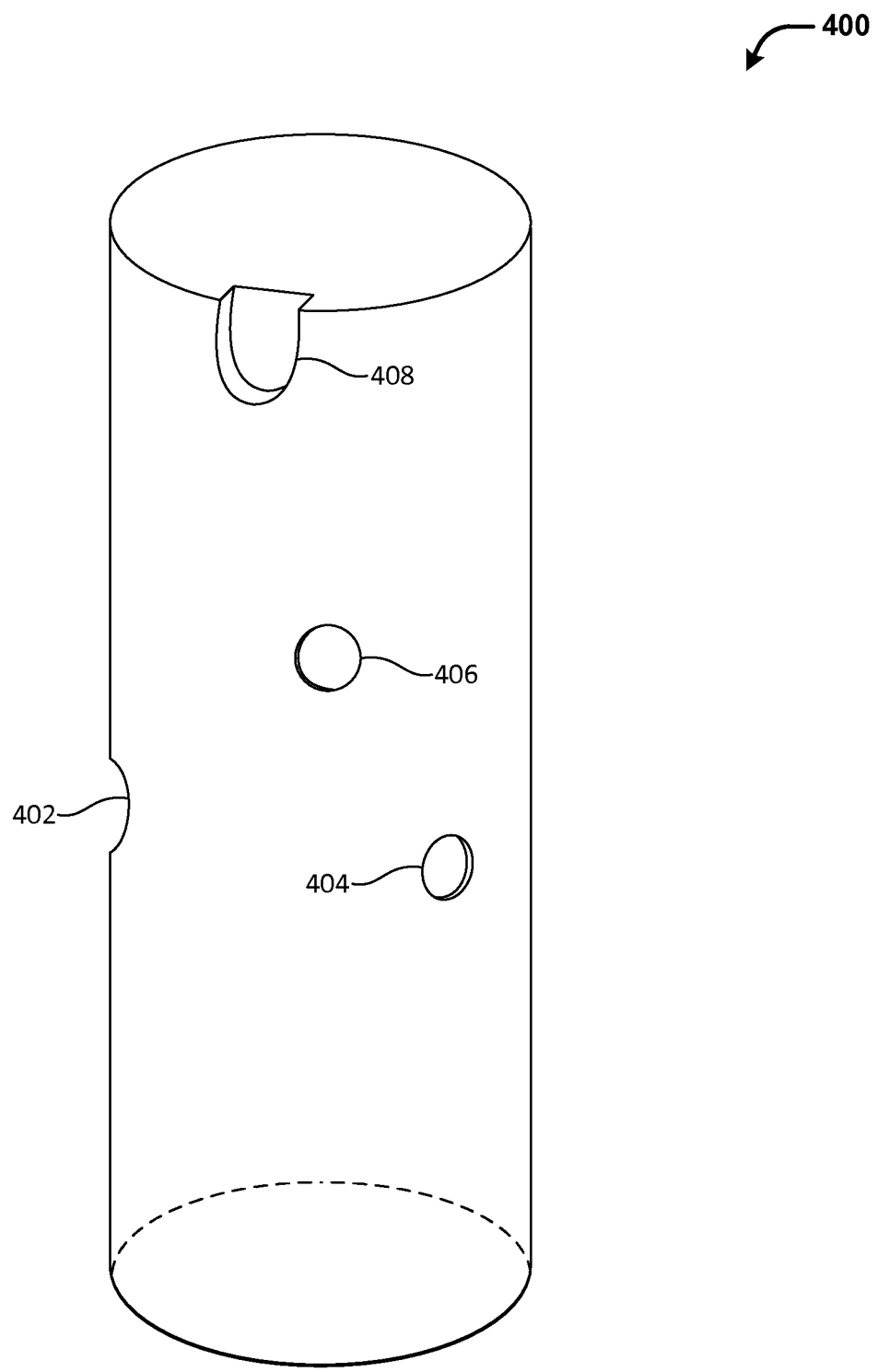
FIG. 4 illustrates another example fenestration template that may be used to generate fenestrations on a stent graft, in accordance with at least one embodiment.

FIG. 4 illustrates another example fenestration template 400 that may be used to generate fenestrations on a stent graft, in accordance with at least one embodiment. For example, the fenestration template 400 may be used to generate fenestrations illustrated in FIG. 2. The fenestration template 400 may be similar to the fenestration template 300 discussed in connection with FIG. 3, except that the fenestration template 400 has a solid cylinder shape instead of a tubular shape as fenestration template 300. The fenestration template 400 may have holes 402, 404, 406 and 408 that corresponds to the openings for branch vessels in the aorta, similar to openings 302, 304, 306 and 308 of fenestration template 300 shown in FIG. 3. In various embodiments, the dimensions of the fenestration template including the diameters of the holes and/or template may be determined based on the dimensions of the aorta or one or more predefined values. When in use, in some embodiments, the fenestration template may be slid into the lumen of a stent graft so that the fenestration template overlaps with a portion of the stent graft where fenestration is required.

Figure 5A:
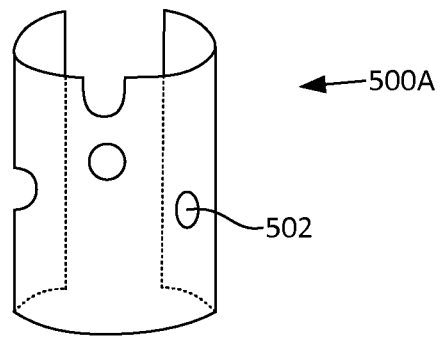
FIGS. 5a-f illustrate some examples of fenestration templates, in accordance with some embodiments.

FIGS. 5a-f illustrate more examples of fenestration templates, in accordance with some embodiments. For example, as shown in FIG. 5a, instead of a tubular shape, the fenestration template 500A can have a partial tubular shape (e.g., semi-circular) with an opening along a longitudinal axis. In some embodiments, the fenestration template may be made of an elastic or resilient material such that the fenestration template may open along the longitudinal axis and clasp around a portion of a stent graft. In other embodiments, the fenestration template may be made of a rigid material and the fenestration template may slide over or into a stent graft in a similar fashion as discussed in connection with FIG. 3.

Figure 5B:
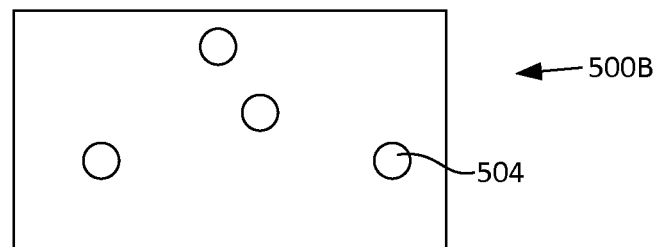

As shown in FIG. 5b, in some embodiments, the fenestration template 500B can be a flat sheet with holes 504 corresponding to the openings of branch vessels on an aorta. In some embodiments, the fenestration template may be made of any elastic material such as paper, metal foil, plastic film, and the like. In some embodiments, the flat sheet may be made of biocompatible graft material. When in use, the fenestration template may be wrapped around a portion of a stent graft that needs to be fenestrated such that the holes 504 on the fenestration template may be used to produce the required fenestrations. In some embodiments, where biocompatible graft material is used as fenestration template, the fenestration template may be wrapped around uncovered stents to produce a fenestrated stent graft. In some embodiments, the fenestration template may include one or more markings (e.g., circles) designating the branch vessels instead of or in addition to the holes.

Figure 5C:
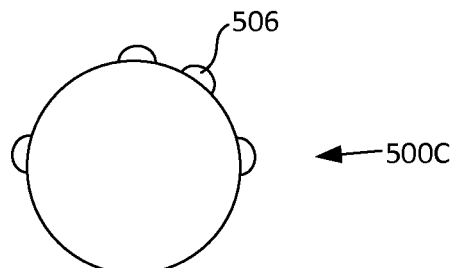

In some embodiments, such as shown in FIG. 5c, the fenestration template may include one or more bumps or protruding structures instead of or in addition to holes or markings to designate the locations of the fenestrations on the stent graft. The protruding structure may be used to mark and/or cut the graft material for fenestration purposes. In some embodiments, the fenestration template 500C may include one or more protruding structures on the outer surface of the template. When in use, in an embodiment, the fenestration template 500C may be placed inside the lumen of a stent graft such that the template overlaps with a portion of the stent graft to be fenestrated.

Figure 5D:
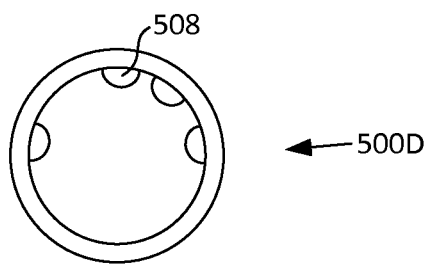

In some other embodiments, such as shown in FIG. 5d, the fenestration template 500D may include one or more protruding structures on an inner surface of the template. When in use, in an embodiment, the fenestration template 500D may be placed outside a stent graft such that the template overlaps with a portion of the stent graft to be fenestrated.

Figure 5E:
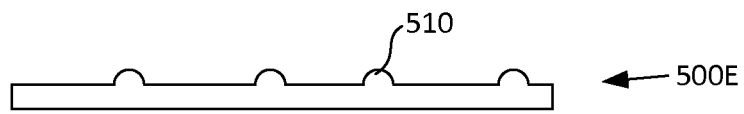

As shown in FIG. 5e, in some embodiments, the fenestration template 500E may be similar to fenestration template 500B discussed in connection with FIG. 5b except that the holes are replaced by protruding structures such as discussed in connection with FIGS. 5c and d. When in use, in an embodiment, the fenestration template 500E may be wrapped around a portion of a stent graft to be fenestrated such that the protruding structures point against or away from the stent graft.

Figure 5F:
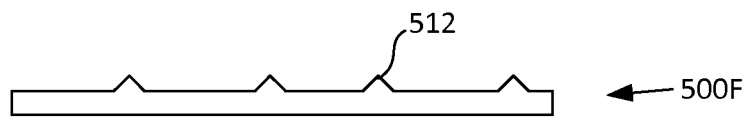

In various embodiments, the protruding structures discussed above may be of any suitable dimensions and/or shapes. For example, the protruding structure may have a semi-circular shape as shown in FIGS. 5c and 5d. For another example, the protruding structure may have a pointed tip as shown in FIG. 5f.

In some embodiments, the protruding structures may be configured to mark locations of the fenestrations on the stent graft material upon contact. Alternatively or additionally, the protruding structures may be configured to produce fenestrations on the stent graft material, for example, using thermal, mechanical, chemical, or other means. For example, the protruding structures may be heated (e.g., electrically) to act as thermal cautery tools for generating holes in the graft material. For another example, the protruding structures may have sharp tips usable for puncturing apertures in the graft materials.

In various embodiments, the fenestration templates may be made of one or more suitable materials, rigid or non-rigid, such as thermoplastic, plaster, metal alloy, titanium alloy, paper, metal foil, plastic film, photopolymer, and the like. In some embodiments, a smooth coating material may be applied to a surface (e.g., lumen wall or outer surface) of the fenestration template to facilitate easier interfacing with a stent graft.

In various embodiments, various aspects of the fenestration templates such as the dimensions of the holes, openings, protruding structures, and the like, the dimension of the template and the like may be determined based on the dimensions of the actual aorta or branch vessels or configurable (predefined) values.

In various embodiments, the fenestration templates may be manufactured using any suitable technologies such as 3-D printing or additive prototyping/manufacturing technologies, subtractive manufacturing techniques, 2-D printing, and the like or a combination thereof. In some embodiments, the fenestration templates are generated for patient-specific anatomy, for example, based on patient-specific imaging data as discussed below.

Figure 6:
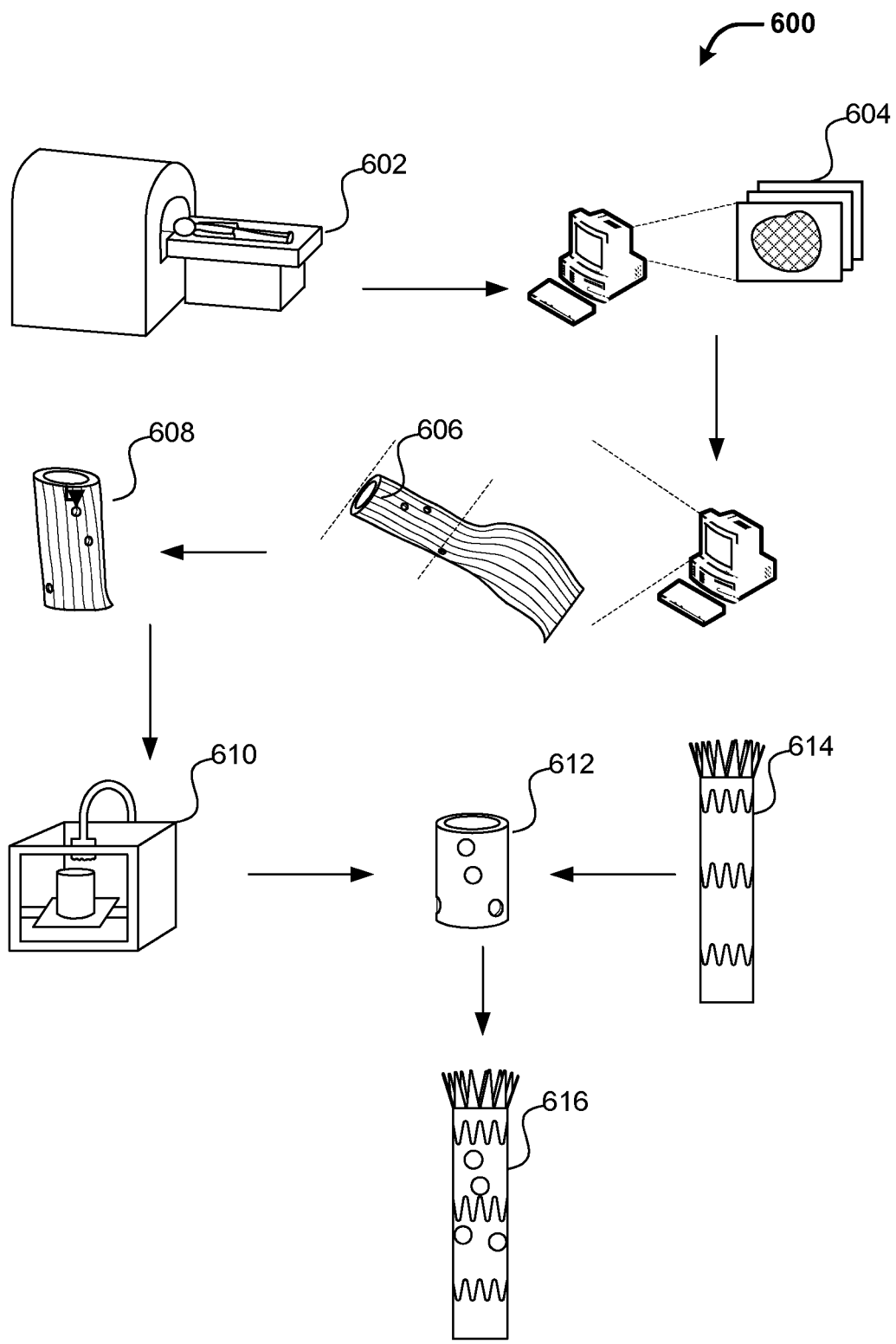
FIG. 6 illustrates an example process for treating aortic aneurysm using a stent graft that is fenestrated using a patient-specific fenestration template, in accordance with at least one embodiment.

FIG. 6 illustrates an example process 600 for treating aortic aneurysm using a stent graft that is fenestrated using a patient-specific fenestration template, in accordance with at least one embodiment. In this example, a patient for endovascular repair of an aortic aneurysm may undergo a scan 602 or a similar imaging procedure to obtain imaging data for a portion of a patient's body. For example, a patient with AAA may receive a contrast-enhanced spiral abdominal/pelvic CT scan in preparation for the endovascular repair procedure. In various embodiments, any suitable medical imaging technologies may be used to obtain the imaging data. Examples of various imaging procedures include x-ray radiology, computed tomography (CT) or computed axial tomography (CAT) scan, ultrasound scan, magnetic resonance imaging (MRI), positron emission tomography (PET), and the like or any combination thereof.

In an embodiment, imaging data 604 (such as CT scan data set) resulting from such an imaging procedure may be obtained and processed, for example, by one or more computer systems, to generate an overall 3-D digital model 606 of an aorta segment. The aorta segment may include a portion where the endovascular repair procedure will take place (e.g., where a stent graft will be deployed). In some embodiments, a second 3-D digital model 608 representing an aorta segment encompassing one or more branch vessels may be extracted from the overall 3-D digital model 606. For example, the second digital model may represent an aorta segment proximal to an abdominal aortic aneurysm. The second 3-D digital model 608 may be used to generate the fenestration template. In other embodiments, the overall 3-D model 606 may be used to generate the fenestration template.

In various embodiments, any number of 3-D digital models may be generated based on a given set of patient imaging data. For example, in some embodiments, two or more 3-D digital models may be generated, each representing a different aorta segment where a different set of branch vessels need to be accommodated. The two or more 3-D digital models may be used to generate two or more fenestration templates, each used to generate fenestrations on different portions of the same stent graft or different stent grafts used on the same patient. For example, a stent graft may be configured to extend from above the renal arteries to below the IMA. In this case, the proximal portion of the stent graft may need to accommodate the renal arteries, SMA and/or the celiac artery, whereas the middle or distal portion of the stent graft may need to accommodate the IMA. As such, two fenestration templates may be required to generate fenestrations for the above two aorta segments (one for accommodating the rental arteries, SMA and/or the celiac artery, one for accommodating the IMA). For another example, a bifurcated stent graft may be configured to extend from above the renal arteries into the iliac arteries. In this example, the stent graft may need to additionally accommodate the internal iliac arteries located towards the distal ends of the stent graft. As such, two or more separate or more fenestration templates may be required (one for accommodating the renal arteries, SMA and/or celiac artery, one for accommodating the IMA, and zero, one or two for accommodating the internal iliac arteries). For example, if the bifurcated stent graft includes a short leg and a long leg each extending into an iliac artery, a fenestration template may be required for the long leg if it occludes a branch vessel such as an internal iliac artery. If the bifurcated stent graft includes two long legs, two fenestration templates may be required, each for one of the long legs if they occlude any branch vessels. Finally, if the bifurcated stent graft includes two short legs, no fenestration template may be required if neither of the short legs occlude any branch vessels.

Generally speaking, extracting only a portion of the overall 3-D digital model rather than using the overall 3-D digital model to generate the fenestration template advantageously reduces the data that needs to be transmitted, stored and/or processed and the resources used for the above. For example, the shorter the fenestration template, the less time and resources (e.g., computing resources and materials) it may take to manufacture the template. In some cases, the shorter fenestration template may also make it easier to couple and/or decouple the template and the stent graft.

Still referring to FIG. 6, in some embodiments, the 3-D digital model of the aorta segment encompassing branch vessels of interest is used by 3-D printing technologies 610 or other additive manufacturing technologies to generate a corresponding fenestration template 612. Examples of the fenestration template 612 may include those fenestration templates described in connection with FIGS. 3-5.

In some embodiments, the fenestration template 612 may be used in conjunction with an unfenestrated stent graft 614 to generate holes or fenestrations that correspond to openings of a patient's actual aorta branch vessels. In some embodiments, the stent graft 614 may include a commercially available, off-the-shelf stent graft. In some embodiments, the fenestration template 612 may be coupled to (e.g., being slid over or into) the stent graft 614 such that the fenestration template overlaps with a branch-vessel-encompassing portion of the stent graft 614. For example, the fenestration template may be placed to overlap with a proximal seal zone of the stent graft. In some embodiments, the overall 3-D digital model 606 may be used directly to generate a fenestration template that extends beyond the aorta segment with branch vessels. In some embodiments, the fenestration template may be sterilized before and/or after being used with the stent graft.

In some embodiments, the positions of the fenestration template and/or the stent graft may be adjusted relative to each other after being coupled to optimize the fenestration process. For example, the fenestration template and/or the stent graft may be moved or rotated relative to the other to avoid positioning holes or fenestrations over the stent struts.

In some embodiments, the stent graft may be fenestrated with the fenestration template in place. In some other embodiments, the locations of the fenestrations may be marked (e.g., using a sterile pen) on the stent graft and the fenestrations may be made after the fenestration template is removed from the stent graft. In yet other embodiments, a combination of above approaches may be used. For example, some fenestrations may be made while the fenestration template is still coupled to the stent graft while other fenestrations may be made after the fenestration template is removed from the stent graft. Eventually, the fenestrated stent graft 616 may be deployed to the patient's aorta during an endovascular repair procedure. During the deployment, the fenestrations in the stent graft would preferably line up with openings of aorta branch vessels to accommodate the flow.

Advantageously, the fenestration template assures that the angular and longitudinal placement of fenestrations accurately matches that of the aorta branch vessel origins because the fenestration template is generated from images of the patient's aorta. Additionally, time is saved both in pre-operative planning, and also in the operating room because the relative distances of the openings are established by the fenestration template. In other words, the surgeons are no longer required to perform any measurements at the time of device deployment of the stent graft. To summarize, the benefits of the fenestration methods described herein include, but are not limited to a) availability of endovascular repair, which has significantly less mortality and morbidity than open repair, to more patients; b) improved outcomes of endovascular repair for juxtarenal aneurysms due to more accurate placement of the branch vessel openings; and c) cost savings due to reduced pre-operative planning time and reduced procedure time.

Figure 7:
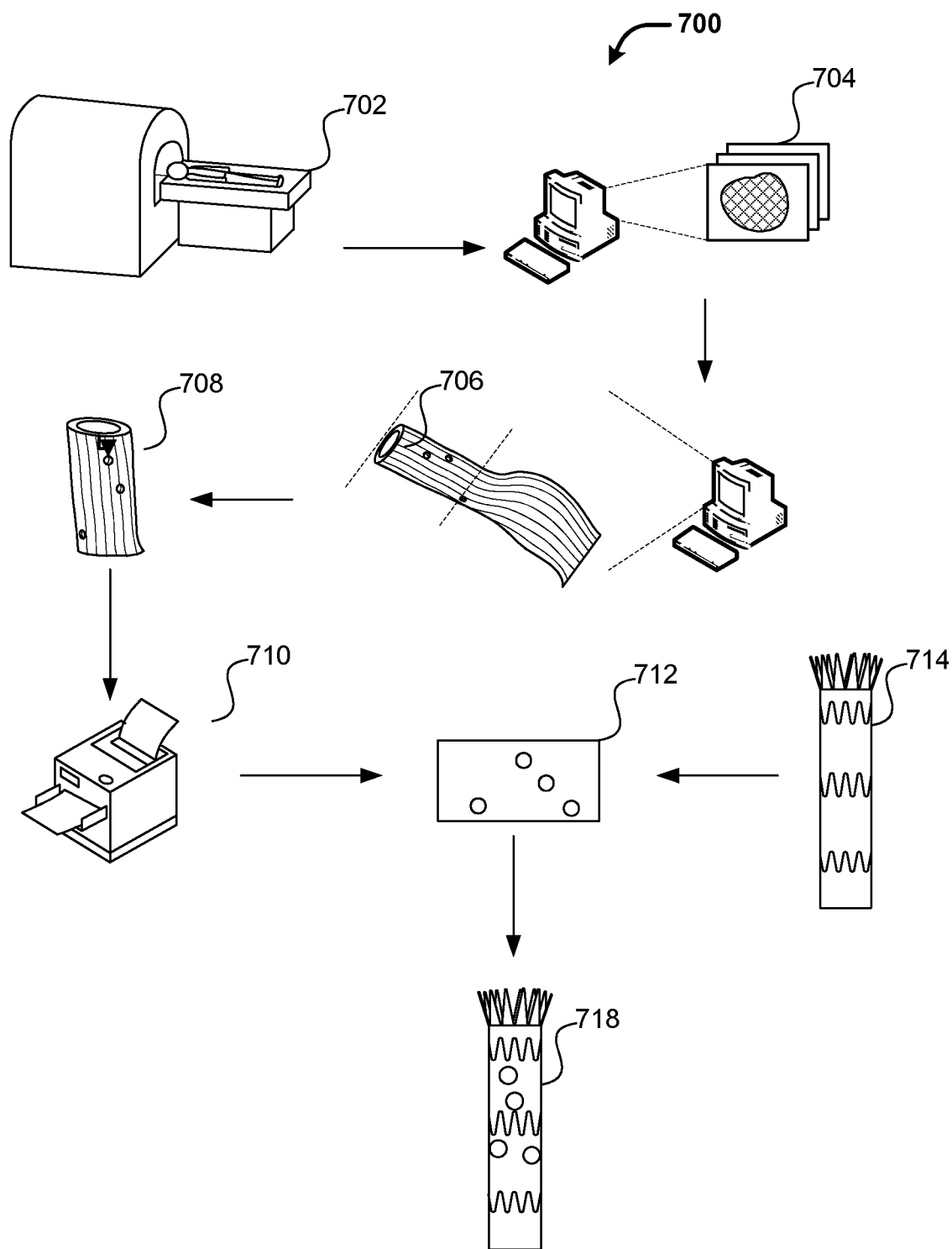
FIG. 7 illustrates an example process for the treating aortic aneurysm using a stent graft that is fenestrated using a patient-specific fenestration template, in accordance with at least one embodiment.

FIG. 7 illustrates an example process 700 for the treating aortic aneurysm using a stent graft that is fenestrated using a patient-specific fenestration template, in accordance with at least one embodiment. The process 700 is similar to the process 600 described in connection with FIG. 6 except that instead of a 3-D solid object generated using a 3-D technology such as described in FIG. 6, a flat sheet with holes or markings may be generated as the fenestration template. Examples of the flat sheet fenestration template 712 may include those described in connection with FIGS. 5b, 5e and 5f. For example, the fenestration template may include a piece of paper, metal foil, plastic film or the like.

In some embodiments, the flat sheet fenestration template may be generated using conventional 2-D printing technologies 710. Alternatively, other manufacturing technologies such as 3-D printing, subtractive manufacturing and the like may be used. In some embodiments, where the fenestration template includes markings designating openings of branch vessels, the fenestration template may or may not be further processed (e.g., to cut holes where the markings are) before being used with a stent graft.

Figure 8:
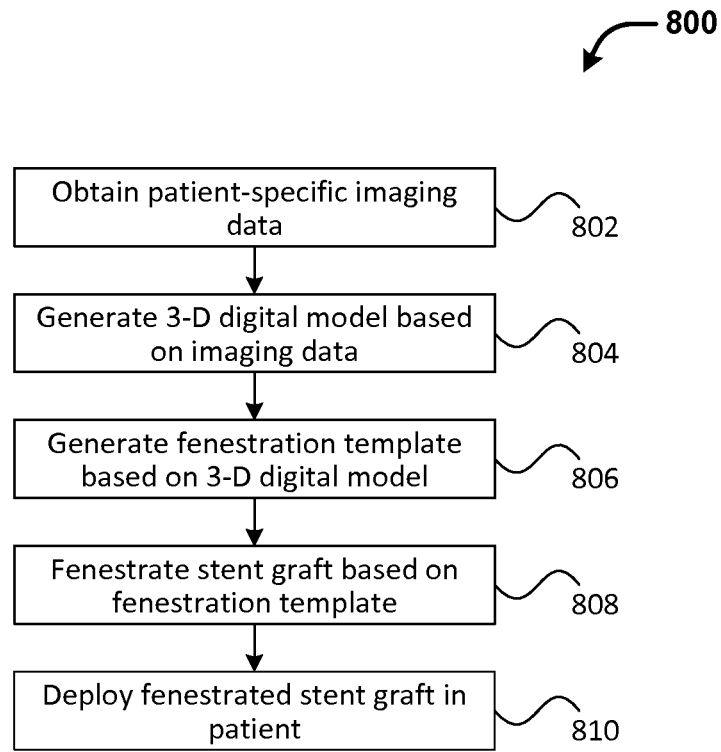
FIG. 8 illustrates an example process for the treating aortic aneurysm using a stent graft that is fenestrated using a patient-specific fenestration template, in accordance with at least one embodiment.

FIG. 8 illustrates an example process 800 for the treating aortic aneurysm using a stent graft that is fenestrated using a patient-specific fenestration template, in accordance with at least one embodiment. Some or all of the process 800 (or any other processes described herein, or variations and/or combinations thereof) may be performed under the control of one or more computer/control systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. The order in which the operations are described is not intended to be construed as a limitation, and any number of the described operations may be combined in any order and/or in parallel to implement the processes.

In an embodiment, the process 800 includes obtaining 802 patient-specific imaging data for a patient with an aneurysm. The imaging data may be obtained based on one or more CT, ultrasound, MRI scans, or the like, or a combination thereof. In some embodiments, the imaging data may be obtained as part of a diagnostic procedure. Once obtained, patient-specific imaging data is used to generate 804 a 3-D digital model of the surface of the patient's aorta lumen such as described in connection with FIG. 6. The 3-D surface model may or may not encompass at least a portion of the aortic aneurysm.

In some embodiments, the 3-D digital model may include openings corresponding to branch vessels originating from the aorta lumen. Boundaries for such branch vessels may be manually or automatically detected and/or calculated based on the imaging data. For example, axial distance of a renal artery along an aorta center line may be measured. As another example, angular position of a branch artery origin may be measured in a transverse image plane. In some embodiments, such indications of such branch vessels may be added to the 3-D digital model (e.g., as openings) using computer aided design (CAD) software. For example, branch vessel coordinates captured from the CT images may be imported and used to mark the origins and orientations of the vessels. Subsequently, a subtraction between the solid part model and a cylinder with a desired fenestration diameter may be performed to create the openings in the 3-D surface model. In various embodiments, the diameters of the branch vessel openings on the 3-D digital model may be a predefined value (e.g., 4 mm) and/or may be derived based on the diameters of the actual branch vessels.

In some embodiments, a segment (e.g., proximal neck portion) of a previously-generated 3-D model may be extracted as a separate 3-D model. The extracted segment may span one or more branch vessel origins (e.g., for the celiac artery, SMA, and/or renal arteries). The second 3-D model or the original 3-D model may be used to generate 806 the fenestration template.

In some embodiments, the size of the 3-D digital model used to generate the fenestration template may be modified to optimize the graft fenestration process. Aortic stent grafts are typically oversized by 15% to 20% relative to the lumen diameter in order to produce stable fixation when the deployed graft expands against the vessel wall. This leads to different options for the creation of the fenestration template. Thus, the dimensions of the 3-D digital model (and hence the template) can either replicate the actual aorta diameter and the graft can be constricted to fit inside this template, or the template can be scaled up such that the minimum diameter of the template matches the graft diameter.

In some embodiments, a 3-D surface model may be scaled using an arbitrary or predefined wall thickness (e.g., 5 mm) to allow 3-D printing as a solid model. Computer-implemented methods may be used to create a radially-expanded surface model to define the wall thickness of the fenestration template. In various embodiments, any suitable prototyping or manufacturing techniques (e.g., 3-D printing or additive manufacturing, subtractive manufacturing, 2-D printing) may be used to generate 806 the fenestration template based on the 3-D model.

Once the fenestration template is generated, it may be used to guide the fenestration 808 of a stent graft. For example, in an embodiment, the stent graft may be inserted into the lumen of the fenestration template such that the fenestration template overlaps with a portion (e.g., proximal portion) of the stent graft that needs to be fenestrated. In some embodiments, the positions of fenestration template and/or the stent graft may be adjusted relative to each other to avoid placing the holes on stent struts. For example, the fenestration template and/or the stent grafts may be rotated relative to each other. In some embodiments, the fenestration template may include markings to guide relative positioning of the fenestration template and the stent graft. Such markings may be generated based on the patient-specific imaging data.

In some embodiments, the fenestrations may be generated with the fenestration template still coupled to the stent graft. In other embodiments, the locations of the fenestrations may be marked (e.g., by a sterile pen) and fenestrations may be generated after the fenestration template is removed from the stent graft. Eventually, the fenestrated stent graft is deployed 810 in the patient. In various embodiments, the fenestration process discussed above may be performed before or during an endovascular repair procedure. Performing the fenestration process before an endovascular procedure advantageously saves the time in the operating room. In addition, the techniques described herein offer a simple yet accurate way to generate fenestrations on a stent graft because the fenestration template is generated based on patient-specific imaging data and hence accurately reflects the actual branch vessel origins of the patient's aorta lumen.

Figure 9A:
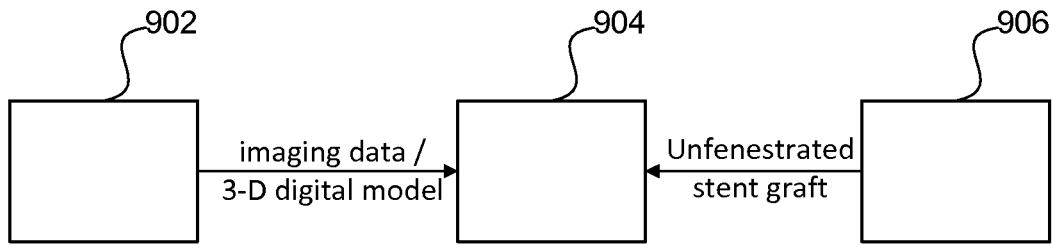
FIGS. 9a-d illustrate example series of communication between various entities involved in a treatment of aortic aneurysm using a patient-specific fenestration template, in accordance with some embodiments.

In various embodiments, techniques described herein may be implemented individually or collectively by one or more entities involved in endovascular repair procedures. FIGS. 9a-d illustrate example series of communication between various entities involved in a treatment of aortic aneurysm using a patient-specific fenestration template, in accordance with some embodiments. As shown in FIG. 9a, in an embodiment, a surgical facility 904 (such as a hospital or clinic) where an endovascular repair procedure is to be performed may obtain patient imaging data from a medical imaging data provider 902.

The medical imaging data provider 902 may be capable of performing a medical scan (e.g., CT scan, ultrasound, MRI, PET) on patients and providing the resulting imaging data (such as CT scan data sets). In some embodiments, the imaging data provider 902 may further process the imaging data, for example, to generate a 3-D digital model, to identify coordinates of aorta branch vessel locations and the like.

Based on the imaging data from the patient, a 3-D digital model of a patient's aorta as well as a fenestration template based on the 3-D digital model or a segment thereof may be generated at the surgical facility 904. Using the fenestration template, an unfenestrated stent graft, such as a commercially available, off-the-shelf stent graft provided by a medical device provider 906 may be fenestrated according to the techniques described herein. In this embodiment, the 3-D digital model generation, fenestration template generation and fenestration process are all performed at the surgical site, thereby advantageously saving the time required to obtain the fenestrated stent grafts. For example, on-site printing at high-volume trauma centers may allow the use of the present template method for emergency cases, especially as 3-D printers become faster and more widely available.

Figure 9B:
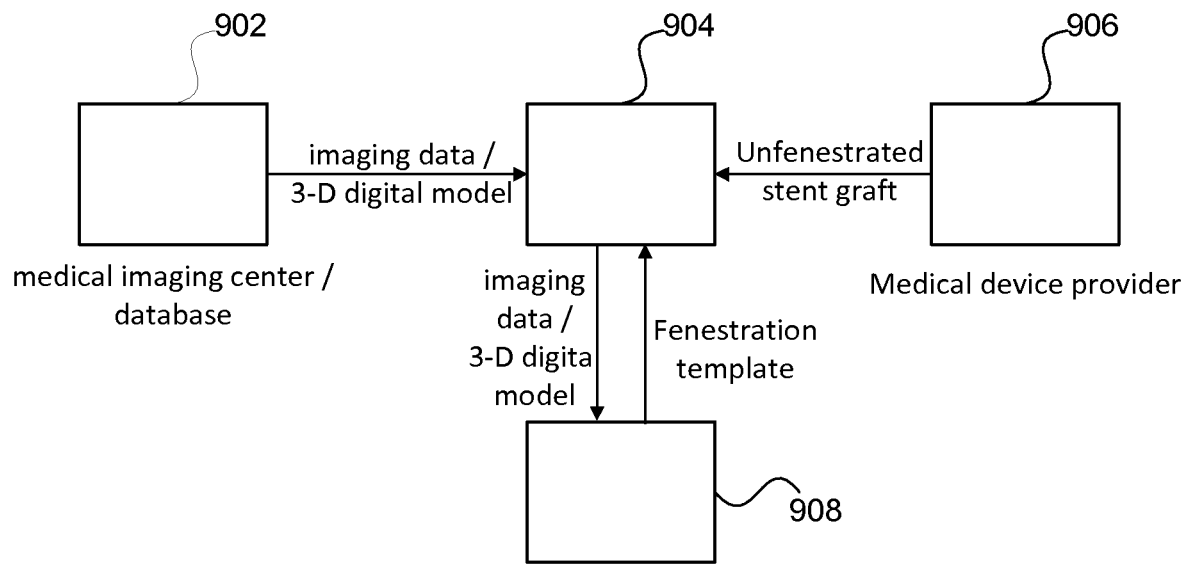

FIG. 9b illustrates another example series of communication between various entities involved in the treatment of aortic aneurysm, in accordance with at least one embodiment. Similar to FIG. 9a, a surgical facility 904 receives patient imaging data and/or 3-D digital model from an imaging service provider 902 and an unfenestrated stent graft from a medical device provider 906. However, in this example, the surgical facility 904 may outsource the data processing (3-D digital model generation) and/or the fenestration template generation process to one or more separate processing facilities 908. For example, the surgical facility 904 may transmit the raw image data (e.g., CT data set), segmented aorta boundaries and/or fenestration locations to a data processing facility 908 which may generate a 3-D digital model with openings corresponding to the branch vessels of interest and/or a fenestration template based on the 3-D digital model. Advantageously, the surgical facility 904 is relieved from having expertise with respect to image data processing, 3-D printing or the like. Accordingly, such an approach may lead to widespread use of fenestrated endovascular stent graft for both elective repairs and treatment of symptomatic AAAs, thus improving patient care and/or reducing cost.

Figure 9C:
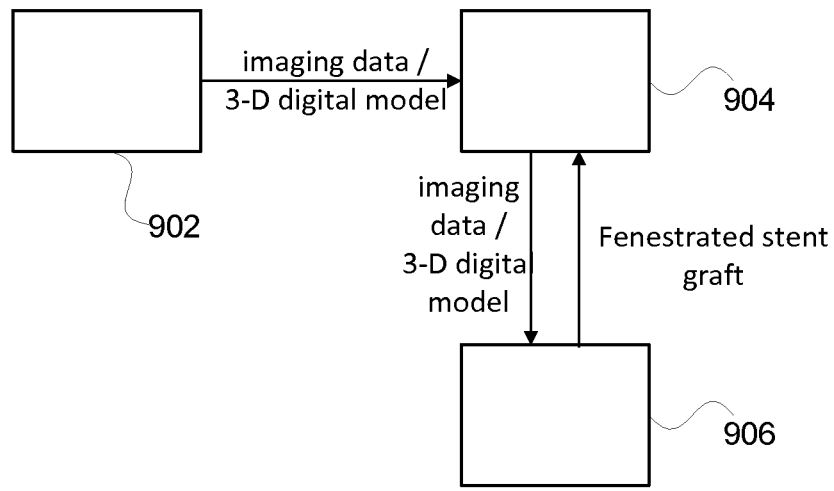

FIG. 9c illustrates another example series of communication between various entities involved in the treatment of aortic aneurysm, in accordance with at least one embodiment. In this example, a surgical facility 904 receives a patient's imaging data from an imaging data provider 902. The surgical facility 904 may or may not further process the imaging data, for example, to identify branch vessel boundaries, generate a 3-D digital model of the aorta and the like. The imaging data and/or other data may be provided to a processing facility 906 that provides a fenestrated stent graft to the surgical facility 904. In an embodiment, the processing facility 906 generates a 3-D digital model of the patient's aorta based on the received imaging data and also generates a fenestration template based on the 3-D digital model. In another embodiment, the processing facility 906 receives a 3-D digital model from the surgical facility 904. Based on the 3-D digital model, the processing facility 906 generates a fenestration template, which may be used by the surgical site 904 to guide the fenestration of the stent graft. Advantageously, the surgical facility 904 is relieved from expertise with respect to the fenestration process.

Figure 9D:
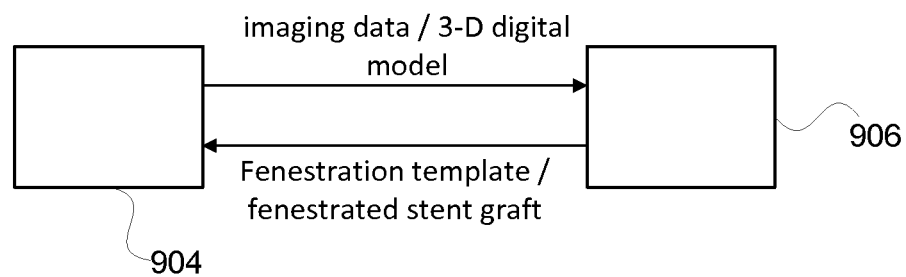

FIG. 9d illustrates another example series of communication between various entities involved in the treatment of aortic aneurysm, in accordance with at least one embodiment. In this example, a surgical facility 904 may have the capacity to acquire a patient's imaging data (e.g., via CT scans). Additionally, the surgical facility 904 may or may not have the capacity to process the imaging data, for example, to identify branch vessel boundaries, generate a 3-D digital model of the aorta and the like. The surgical facility 904 may send the imaging data and/or any processed imaging data such as a 3-D digital model of the patient's aorta lumen to a separate processing facility 906, which may or may not further process the imaging data (e.g., to obtain the 3-D digital model of the patient's aorta based on the imaging data). The processing facility 906 may provide a fenestration template to the surgical facility 904 based on the 3-D digital model. Alternatively or additionally, the processing facility 906 may also provide a fenestrated stent graft where the fenestrations are generated using the fenestration template.

In various embodiments, various aspects of the methods described herein such as imaging data collection, data processing, fenestration template generation, stent graft fenestration and the like may performed individually or collectively by any number of entities. In various embodiments, the data exchange between the various entities described above may be via any suitable public or private data network such as the Internet, local area network (LAN), cellular network and the like.

Figure 10:
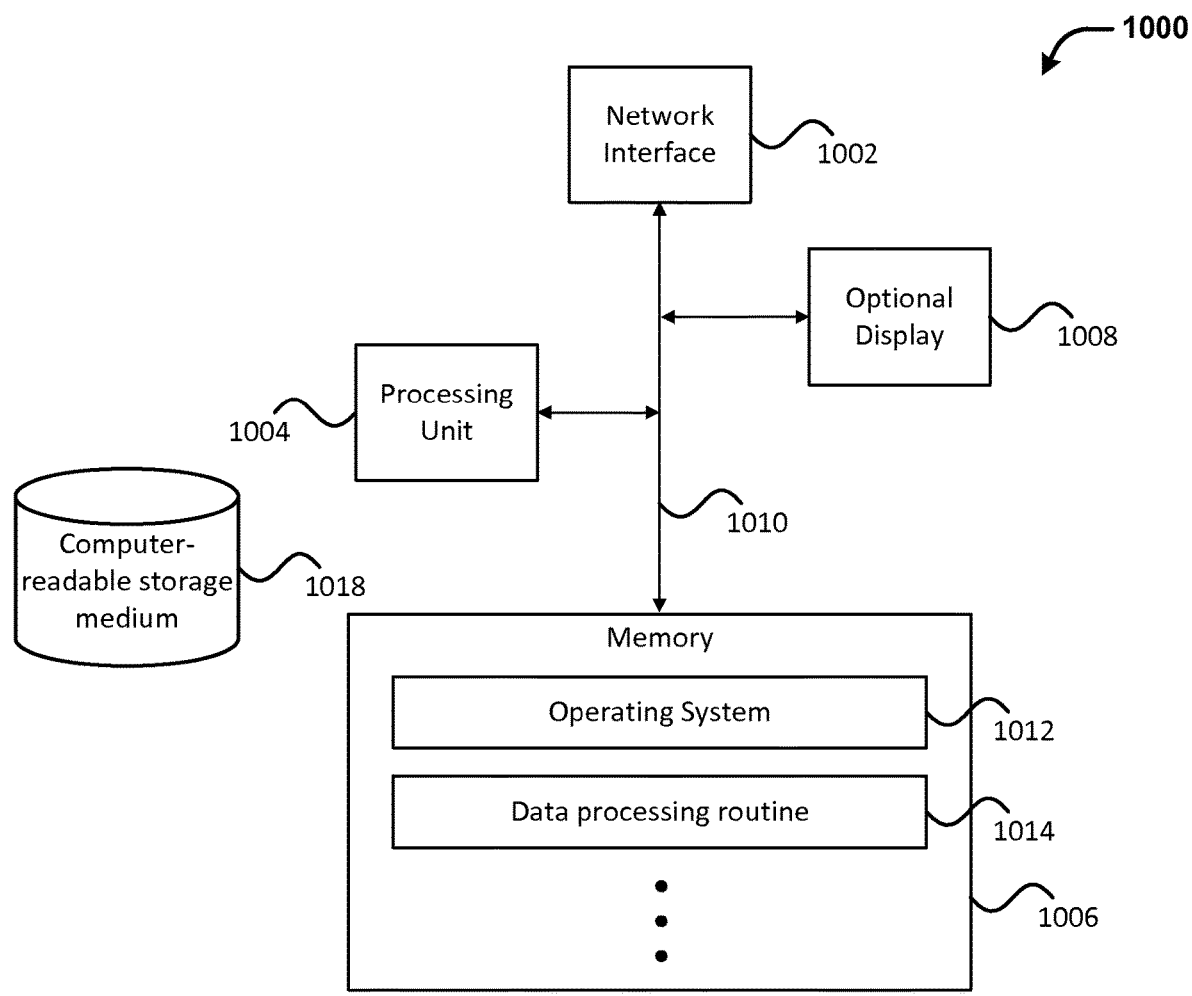
FIG. 10 illustrates example components of a computer device or computer system for implementing aspects of the present invention, in accordance with at least one embodiment.

FIG. 10 illustrates example components of a computer device or computer system 1000 for implementing aspects of the present invention, in accordance with at least one embodiment. In some embodiments, computing device 1000 may include many more components than those shown in FIG. 10. However, it is not necessary that all of these generally conventional components be shown in order to disclose an illustrative embodiment.

As shown in FIG. 10, computing device 1000 includes a network interface 1002 for connecting to a network such as discussed above. In various embodiments, the computing device 1000 may include one or more network interfaces 1002 for communicating with one or more types of networks such as IEEE 802.11-based networks, cellular networks and the like.

In an embodiment, computing device 1000 also includes one or more processing units 1004, a memory 1006, and an optional display 1008, all interconnected along with the network interface 1002 via a bus 1010. The processing unit(s) 1004 may be capable of executing one or more methods or routines stored in the memory 1006. The display 1008 may be configured to provide a graphical user interface to a user operating the computing device 1000 for receiving user input, displaying output, and/or executing applications such as computer aided design (CAD) applications.

The memory 1006 may generally comprise a random access memory ("RAM"), a read only memory ("ROM"), and/or a permanent mass storage device, such as a disk drive. The memory 1006 may store program code for an operating system 1012, a data processing routine 1014, and other routines. In some embodiments, the data processing routine 1014 may be configured to process medical imaging data to generate a 3-D digital model of an aorta lumen and/or cause the creation of a fenestration template based on the 3-D digital model.

In some embodiments, the software components discussed above may be loaded into memory 1006 using a drive mechanism (not shown) associated with a non-transient computer readable storage medium 1018, such as a floppy disc, tape, DVD/CD-ROM drive, memory card, USB flash drive, solid state drive (SSD) or the like. In other embodiments, the software components may alternately be loaded via the network interface 1002, rather than via a non-transient computer readable storage medium 1018.

In some embodiments, the computing device 1000 also communicates via bus 1010 with one or more local or remote databases or data stores (not shown) via the bus 1010 or the network interface 1002. Such data stores may be used to store patient imaging data and/or the result of processing of such imaging data such as related to a 3-D digital model. The bus 1010 may comprise a storage area network ("SAN"), a high-speed serial bus, and/or via other suitable communication technology. In some embodiments, such databases or data stores may be integrated as part of the computing device 1000.

Figure 11:
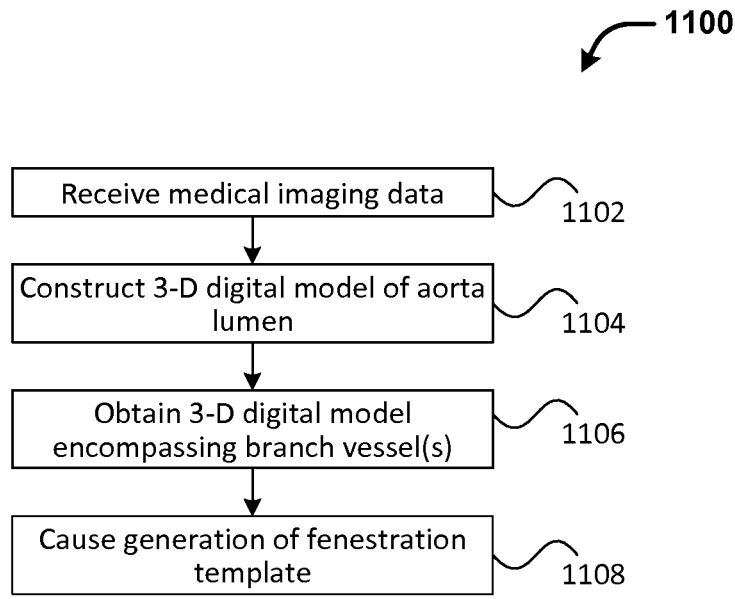
FIG. 11 illustrates an example process for generating a 3-D digital model of an aorta segment, in accordance with at least one embodiment.

FIG. 11 illustrates an example process 1100 for generating a 3-D digital model of an aorta segment, in accordance with at least one embodiment. Aspects of the process 1100 may be performed, for example, individually or collectively by one or more computer system such as computer system 1000 discussed in connection with FIG. 10.

In an embodiment, process 1100 includes receiving 1102 medical imaging data of a patient. Such medical imaging data may pertain to an area of interest such as a patient's aorta where an aneurysm occurs. In various embodiments, the image data may be obtained from one or more diagnostic scans of an area of interest such as CT scans, ultrasound, MRI scans, PET scan, and/or the like or any combination thereof.

Based on the imaging data, a 3-D digital model of an aorta lumen may be constructed 1104, for example, using any suitable volume or surface reconstruction algorithm. In an embodiment, custom image segmentation software may be used to manually outline the 3-D image data sets. For example, the custom image segmentation software may be implemented using MATLAB provided by MathWorks of Natick, Massachusetts. In such embodiments, features of interest may be traced and spline curves may be fit to the user-specified points. In addition, markers can be placed at specific 3-D locations to indicate the origins of the branch vessels. In an embodiment, the outlines are converted to 3-D contours that define the feature locations in the 3-D space. The 3-D contours may be converted to a mesh to define a 3-D surface model. In various embodiments, the custom segmentation software may be configured to obtain different types of imaging data such as CT imaging data, ultrasound data, and the like. In some embodiments, the size of the generated 3-D surface model may be modified to optimize the graft fenestration process. For example, the surface model may be radially expanded to add a predefined wall thickness to allow generation of a solid fenestration template.

Alternatively or additionally to the custom image segmentation software discussed above, a medical visualization tool such as provided by TeraRecon of Foster City, California, may be used to produce 3-D and multi-planar views of CT image sets. In some embodiments, such a visualization tool may be capable of performing automatic vessel boundary detection. In such embodiments, the coordinates of the automatically detected vessel contours or boundaries may be imported into the custom segmentation software that generates the 3-D surfaces to expedite the model generation and hence the fenestration generation process. In yet some other embodiments, such visualization tools may be used to automatically generate the 3-D surface data required for the digital model and/or the fenestration template. Once the vessel boundaries are identified, various methods may be used to create corresponding openings in the 3-D digital model. In an embodiment, a subtraction between the solid part model and a cylinder with the desired fenestration diameter is performed to create the openings in the 3-D digital model. In another embodiment, holes representing the origins of branch vessels may be added using a computer aided design (CAD) software program such as FreeCAD available under the GNU General Public License.

Advantageously, the availability of automatic aorta boundary detection makes the creation of the present fenestration guide a practical option for routine use in endovascular aortic aneurysm repair. Raw imaging data or the segmented aorta boundaries and fenestration locations may be sent to an outside processing facility, and the fenestration guide shipped back to the surgery site. Therefore, individual clinical sites do not require expertise with image segmentation, CAD software or a 3-D printer. This approach may lead to widespread use of fenestrated stent grafts for both elective repairs and treatment of symptomatic AAAs, thus improving patient care and reducing cost.

Still referring to FIG. 11, in some embodiments, a second 3-D digital model encompassing one or more branch vessels may be obtained 1106 from a first 3-D digital model of the aorta lumen such as discussed above. For example, the second 3-D digital model may be obtained by extracting the proximal neck portion of the first 3-D digital model. Such a second 3-D digital model may include the vessel origins of one or more aorta branch vessels such as the celiac artery, SMA, renal arteries and the like. In some embodiments, the second 3-D digital model may be used to generate the fenestration template. In other embodiments, a second, separate 3-D digital model is not created. Instead, the first 3-D digital model is used directly to generate the fenestration template.

In an embodiment, the process 1100 includes causing 1108 the fenestration template to be generated based on a 3-D digital model of an aorta segment. Such a 3-D digital model may include a first 3-D digital model originally generated, a second 3-D digital model extracted from the first 3-D digital model, or any other 3-D digital model. In an embodiment, such a 3-D digital model is first converted to a solid object model format such as stereolithography (STL) or Virtual Reality Modeling Language (VRML) that is supported by a 3-D printer or similar template generation device. In an embodiment, a CAD program such as SolidWorks Professional provided by Dessault Systemes SolidWorks Corp. of Waltham, Massachusetts, may be used to convert a 3-D digital model to a solid part format. In another embodiment, no such conversion may be required. In some embodiment, the solid object model may be provided (e.g., transmitted electronically) to a device capable of generating the corresponding fenestration template.

In various embodiments, the template size, wall thickness, fenestration sizes, and/or other features of the vessel openings template may be optimized and/or selected to accommodate graft oversizing. In particular, openings in the template can be made to match the actual vessel origins, sizes of the stent graft to be used with the template, or set to a standard diameter. In various embodiments, parameters governing various aspects of the process 1100 (e.g., diameters of openings, wall thickness) may be specified by a user, predefined or hard-coded and/or based on data obtained in real-time.

In various embodiments, various prototyping and manufacturing technologies and devices may be used to generate the fenestration template. For example, in an embodiment, a Dimension uPrint 3D printer (provided by Stratasys Ltd of Eden Prairie, Minnesota) is used to create solid parts using Fused Deposition Modeling (FDM) technology. FDM is a two-material process. Filaments of ABSplus modeling material (a thermoplastic) and soluble support material are fed to the uPrint extrusion head. In the uPrint extrusion head, the materials are heated to a semi-liquid state, forced through dual extrusion tips and precisely deposited onto a modeling base in extremely fine layers. The print head moves in a horizontal plane and the modeling base moves downward as the model and its support material are built from the bottom up, layer by layer. After the build is complete, the support material is dissolved away and the model is ready to use or finish if needed. This printing method can produce complex shapes and ABSplus is a strong and durable material used not only in 3D printers for production of working prototypes but also in manufacturing of such items as cell phones and television sets. In some embodiments, the 3-D printers may be capable of producing contorted hollow shapes that are far beyond the complexity that is reasonably expected in an aorta segment.

In another embodiment, a flat sheet fenestration template such as illustrated in FIG. 5b may be generated based on the 3-D digital model of the aorta segment. For example, the flat sheet may represent the outer surface of the aorta segment with holes or markings representing the branch vessel origins. Such a flat sheet template may be scaled according to the actual size of the aorta segment, the size of the stent grafts to be fenestrated or predefined parameters. In various embodiments, the flat sheet template may be made of elastic or pliable material such as paper, metal foil, plastic film or the like. In some embodiments, the flat sheet template may be generated by any suitable device or devices such as a 2-D printer, 3-D printer or the like.

In typical embodiments, the fenestration templates may be disposable. That is, the fenestration template may be used once and then discarded. Accordingly, the templates may not be expected to be subjected to significant forces under normal use or require long-term storage. In some embodiments, the fenestration templates may be reusable and made of a more durable material.

In typical embodiments, the branch vessel origins are represented as openings or holes in the fenestration templates. In alternative embodiments, the branch vessel origins may be represented by protruding structures, markings or the like such as illustrated in FIGS. 5c-f.

Figure 12A:
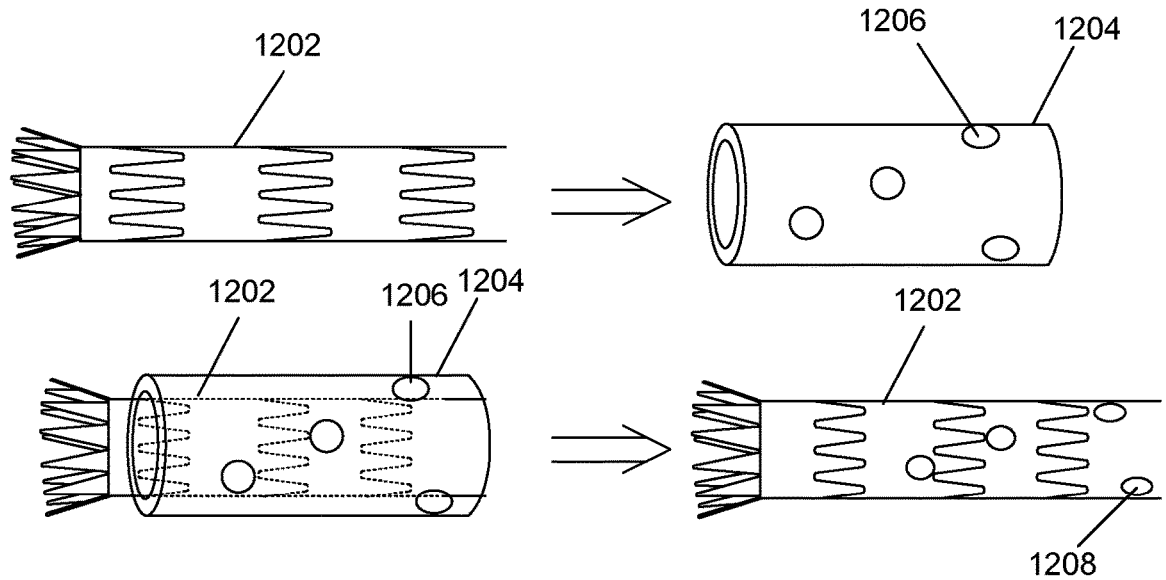
FIGS. 12a-c illustrate example methods for using the fenestration templates to guide the fenestration of stent grafts, in accordance with some embodiments.
Figure 12B:
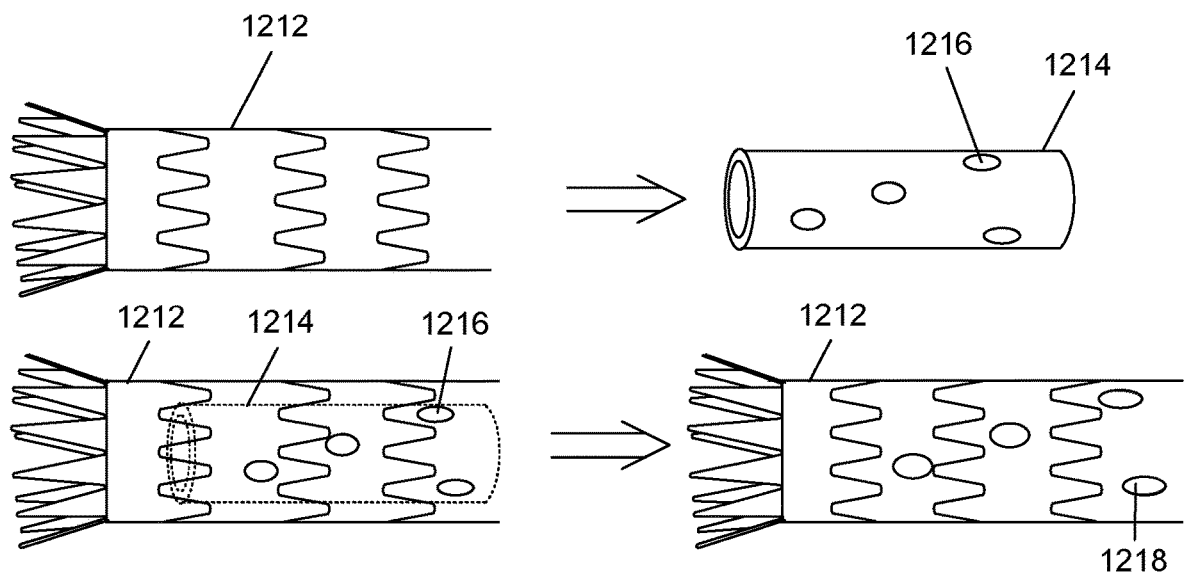
Figure 12C:
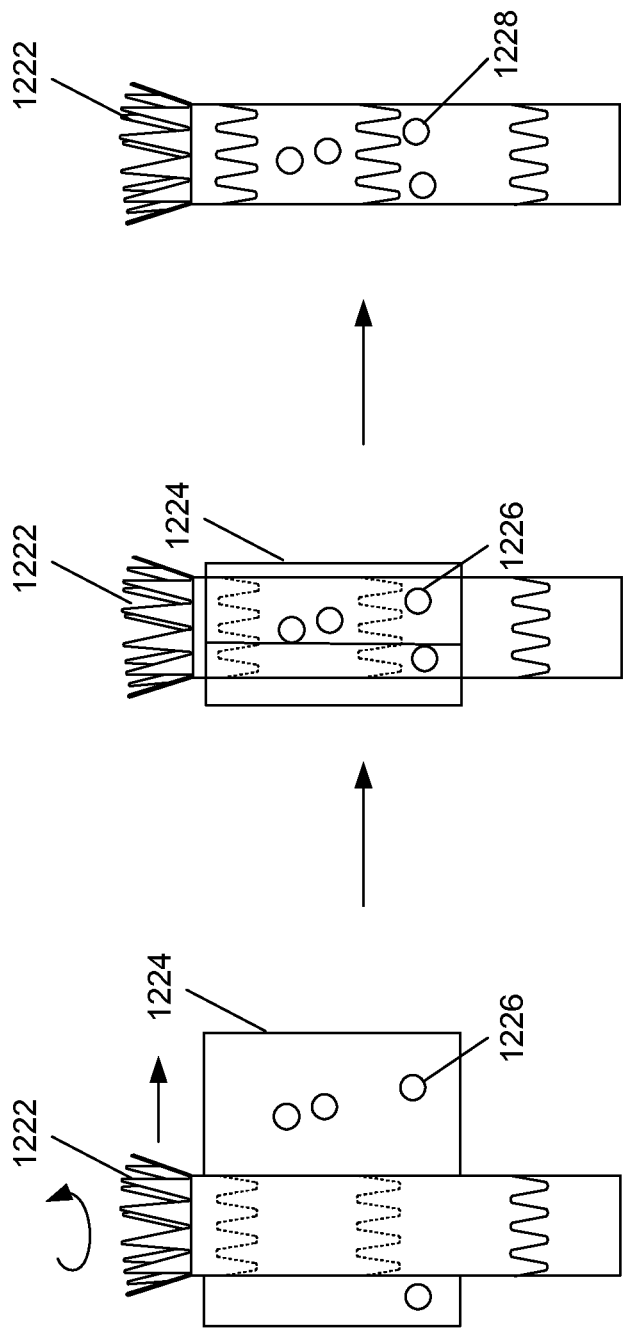

Once the fenestration template is generated, it may be used to fenestrate a stent graft. In various embodiments, the fenestration process may be performed at a clinical site, by a medical device (e.g., stent graft) provider, or any suitable entity. FIGS. 12a-c illustrate example methods for using the fenestration templates to guide the fenestration of stent grafts, in accordance with some embodiments. Advantageously, the fenestration methods described herein may reduce the time and cost associated with a fenestration procedure while increasing its accuracy. In particular, it is relatively fast and easy to determine the locations of the fenestrations using a fenestration template (as shown below) such that to enable a less skilled person to perform the fenestration process. Further, fenestrations generated by using the fenestration template are likely to closely match the branch vessel origins of the patient because the fenestration template is generated based on the actual anatomy of the patient.

In some embodiments, such as shown in FIG. 12a, a stent graft 1202 may be inserted into the lumen of a fenestration template 1204. The fenestration template 1204 includes one or more holes 1206 corresponding to the origins of branch vessels of an aorta. Such holes on the template may be used as a guide for generating fenestrations 1208 on the stent graft. In some embodiments, adjustment may be made to the relative positions of the stent graft 1202 and/or the fenestration template 1204 to optimize the fenestration process. For example, the stent graft 1202 and/or fenestration template 1204 may be moved along a longitudinal axis or rotated relative to each other around the longitudinal axis to avoid placement of template holes over stent struts. In some embodiments, the fenestration template may provide markings or other indications for the positioning of the stent graft relative to the fenestration template.

In some embodiments, such as shown in FIG. 12b, a stent graft 1212 may be slid over a fenestration template 1214. The fenestration template 1214 includes one or more holes 1216 corresponding to origins of branch vessel openings of an aorta. Such holes on the template may be used to as guide for generating fenestrations 1218 on the stent graft. For example, the holes may be visible through the graft material of the stent graft. As in FIG. 12a, adjustment may be made to the relative positions of the stent graft and/or the fenestration template to optimize the fenestration process. In some embodiments, the fenestration template may provide markings or other indications for the positioning of the stent graft relative to the fenestration template.

In some embodiments, the fenestrations may be generated with the fenestration template still engaged or coupled with the stent graft. In other embodiments, the locations of the fenestrations may be marked, for example, with a sterile pen or other marking devices on the stent graft (e.g., through the holes on the fenestration template in FIG. 12a or based on perceived locations of the holes through the graft material in FIG. 12b) and the actual fenestrations on the stent graft may be generated after the fenestration template is decoupled or removed from the stent graft.

In some embodiments, a coating material may be applied to a surface of the fenestration template to allow for smooth rotation or movement of the stent graft relative to the fenestration template. For example, such coating material may be applied to the wall of the lumen of the fenestration template in FIG. 12a or the outer surface of the fenestration template in FIG. 12b. In some cases, such coating material may be used to smooth over small-scale roughness due to the layer-by-layer deposition of the modeling material during 3-D printing. In some embodiments, the coating material may also be compatible with sterilization requirements.

FIG. 12c illustrates another example method for engaging or coupling a stent graft 1222 and a fenestration template 1224 for fenestration purpose. In this example, the fenestration template 1224 is shaped as a flat sheet (such as a piece of paper) corresponding to the outer surface of a patient's aorta. The flat sheet may have one or more holes or markings 1226 that correspond to the origins of one or more branch vessels.

When in use, in an embodiment, the fenestration template 1224 is wrapped around a portion or segment of the stent graft (such as the proximal neck). The locations of fenestrations on the stent graft are marked by the overlapping holes or markings 1226 on the fenestration template. In some embodiments, the fenestration template and/or the stent graft may be adjusted to avoid placing holes on the stent struts. In some embodiments, the fenestration template may provide additional markings indicating where and how the stent graft should be placed relative to the fenestration template.

In some embodiments, once the relative positions of the stent graft and the fenestration template are fixed, the stent graft may be fenestrated according to the holes or markings on the fenestration template while the fenestration template is still coupled to the stent graft. In other embodiments, the locations of the fenestrations 1228 may be marked according to the holes or markings on the fenestration template and the actual fenestrations on the stent graft may be generated after the fenestration template is decoupled or removed from the stent graft.

In some embodiments, the fenestration template may include bumps or protruding structures instead of or in addition to holes to designate the branch vessel origins. In such an embodiment, the fenestration template may be wrapped around the stent graft such that the bumps point towards the graft material. In some embodiments, the protruding structures may be configured to mark locations of the fenestrations on the stent graft material upon contact. Alternatively or additionally, the protruding structures may be configured to produce fenestrations on the stent graft material, for example, using thermal, mechanical, chemical, or other means. For example, the protruding structures may be heated (e.g., electrically) so as to act as thermal cautery tools for generating holes in the graft material. For another example, the protruding structures may have sharp tips usable for puncturing apertures in the graft materials. In yet other embodiments, the fenestration template may be wrapped around the stent graft such that the bumps on the fenestration template face away from the graft material.

Figure 13A:
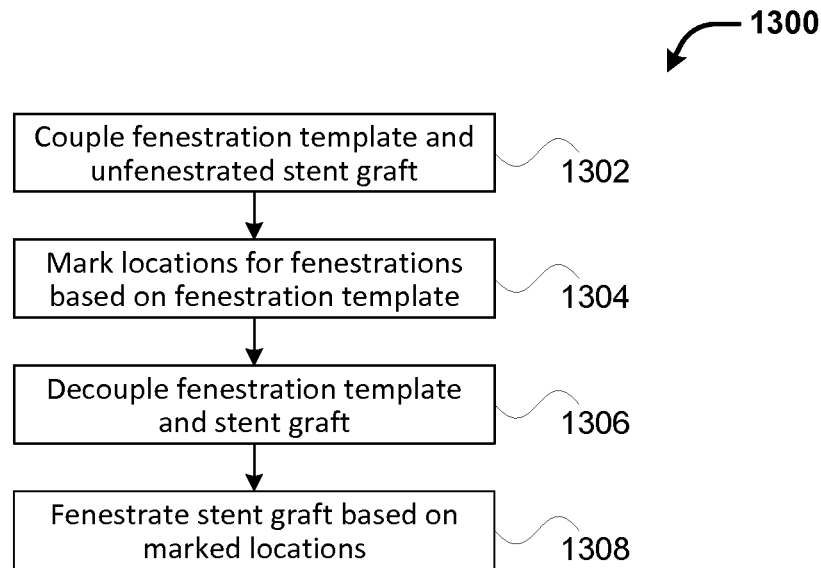
FIGS. 13a-b illustrate example processes for generating a fenestrated stent graft using a fenestration template, in accordance with some embodiments.
Figure 13B:
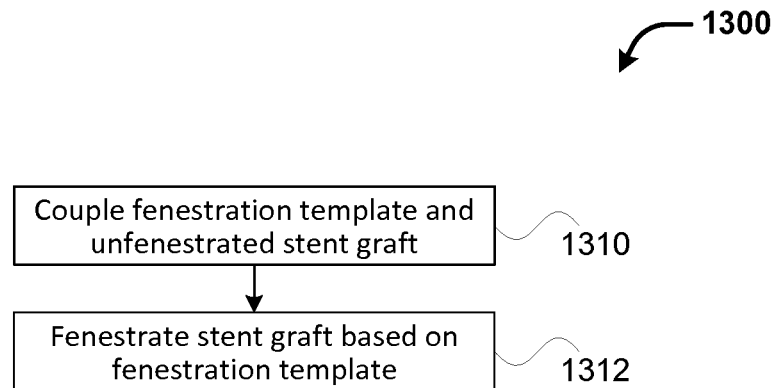

FIGS. 13a-b illustrate example processes 1300 for generating a fenestrated stent graft using a fenestration template, in accordance with some embodiments. As shown in FIG. 13a, in an embodiment, the process 1300 includes coupling 1302 a fenestration template with an unfenestrated stent graft. In various embodiments, the fenestration template and/or the stent graft may be sterilized before and/or after the fenestration process. In various embodiments, the fenestration template may be configured to be coupled with the stent graft in various ways. For example, the fenestration template may be slid over or inserted into the stent graft such as illustrated in FIGS. 12a-b. As another example, the fenestration template may be wrapped around a portion of the stent graft such as illustrated in FIG. 12c. As discussed above, positions of the fenestration template and/or the stent graft may be adjusted relative to each other to optimize the fenestration process, for example, to avoid placing the holes on the stent struts.

In an embodiment, the process 1300 includes marking 1304 the locations for the fenestrations on the stent graft based on the fenestration template. For example, in an embodiment, the locations may be marked through the holes on the fenestration template using a sterile pen. In another embodiment where the fenestration template includes bumps instead of holes, such markings may be made by pressing the bumps on the fenestration template against the graft material.

Once the fenestration locations are marked, the fenestration template and the stent graft may be decoupled 1306. Decoupling may include, in some embodiments, pulling the stent graft out of the fenestration template or vice versa, or unwrapping the fenestration template from the stent graft. Subsequently, fenestrations or holes may be generated 1308 on the stent graft at the marked locations.

FIG. 13b illustrates another example process 1300 for generating a fenestrated stent graft using a fenestration template, in accordance with at least one embodiment. According to this embodiment, the fenestration template is first coupled 1310 to the unfenestrated stent graft similar to step 1302 of FIG. 13a, discussed above. Subsequently, without first decoupling the fenestration template and the stent graft, stent graft may be fenestrated 1312 according to overlapping holes in the fenestration template.

Figure 14B:
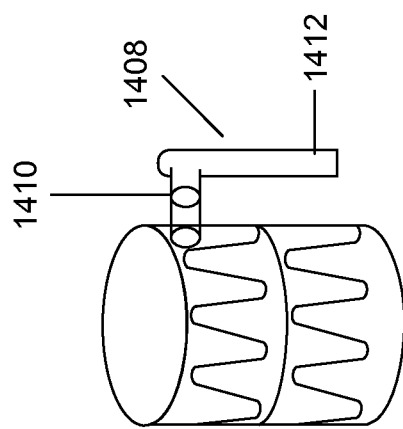
FIG. 14a-b illustrate example devices that may be used to cut holes (fenestrations) on a stent graft, in accordance with some embodiments.
Figure 14A:
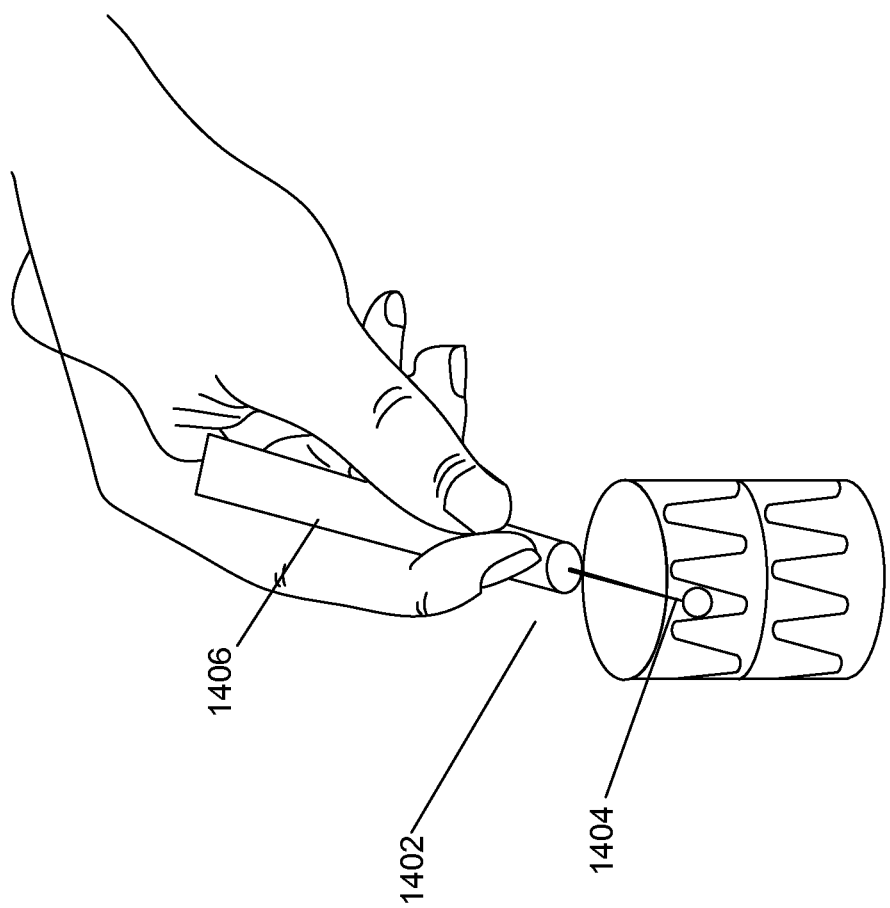

FIG. 14a-b illustrate example devices that may be used to cut holes (fenestrations) on a stent graft, in accordance with some embodiments. In an embodiment such as illustrated in FIG. 14a, a thermal cautery tool 1402 is used to create openings on the graft material. The thermal cautery tool may include a tip or blade 1404 that is heated to cut the graft material and a handle 1406 that may be held by a person (e.g., physician) performing the fenestration process or another device. In various embodiments, various cauterization techniques, such as involving electrocautery, chemical cautery, and the like, may be used.

FIG. 14b illustrates a device 1408 according to another embodiment. The device 1406 may include a substantially circular cutting head 1410 that may be used to cut a hole on the graft material. In an example, the cutting head may be heated around the rim by electric current. The device 1406 may also include a handle 1406 that may be held by a person or another device. In some embodiments, the size (e.g., diameter) of the circular head may be configurable/adjustable based on the desired sizes of the fenestrations.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A computer-implemented method for generating a patient-specific fenestration template, comprising:
   receiving imaging data of a patient;
   generating, based at least in part on the imaging data, a 3-D digital model of an aorta lumen of a patient, the aorta lumen encompassing one or more branch vessels;
   causing generation of the fenestration template based at least in part on the 3-D digital model, wherein the fenestration template represents a model of the aorta lumen without an aneurysm, wherein the fenestration template is cylindrical, wherein a diameter of the fenestration template matches a diameter of the aorta lumen, and wherein generating the fenestration template comprises:
   detecting boundaries for the one or more branch vessels using the imaging data,
   adding indications of the one or more branch vessels to the 3-D digital model, and
   subtracting a cylinder with a desired fenestration diameter from a solid part of the fenestration template to create one or more openings in the fenestration template; and
   scaling up the fenestration template such that a minimum diameter of the fenestration template matches a graft diameter.

2. The computer-implemented method of claim 1, wherein the imaging data includes at least CT scan data, ultrasound data, or MRI data.

3. The computer-implemented method of claim 1, wherein causing generation of the fenestration template includes converting the 3-D digital model to a solid object model format suitable for 3-D printing.

4. The computer-implemented method of claim 1, further comprising:
   generating a second 3-D digital model based at least in part on the 3-D digital model; and
   generating a second fenestration template based at least in part on the second 3-D digital model.

5. The method of claim 1, wherein the fenestration template is a sheet configured to be rolled into a cylinder.

6. The method of claim 5, wherein the method further comprises generating one or more bumps, one or more protrusions, or a combination thereof on the fenestration template.

7. The method of claim 6, wherein the one or more bumps, one or more protrusions, or a combination thereof are configured to produce fenestrations in a stent graft.

8. The method of claim 6, wherein producing fenestrations in the stent graft comprises:
   thermally generating holes in a graft material;
   chemically generating holes in the graft material;
   puncturing holes in the graft material; or
   a combination thereof.

9. A method for treating aortic aneurysm, comprising:
   obtaining a stent graft comprising one or more fenestrations generated using the fenestration template generated with the method of claim 6; and
   deploying the stent graft in the aorta lumen of the patient such that the one or more fenestrations accommodate one or more branch vessels encompassed by the aorta lumen.

10. The method of claim 9, wherein the fenestration template is manufactured using 3-D printing technology.

\* \* \* \* \*